United States Patent [19]

Falch et al.

[11] Patent Number: 5,998,613

[45] Date of Patent: Dec. 7, 1999

[54] 4-AMINOTETRAHYDROBENZISOXAZOLE OR -ISOTHIAZOLE COMPOUNDS

[75] Inventors: Erik Falch, Vedbaek; Jens Kristian Perregaard, Jaegerspris; Arne Schousboe, Ballerup; Povl Krogsgaard-Larsen, Allerod; Bente Frolund, Charlottenlund; Sibylle Moltzen Lenz, Gentofte, all of Denmark

[73] Assignee: H. Lundbeck A/S, Copenhagen-Valby, Denmark

[21] Appl. No.: 08/942,467

[22] Filed: Aug. 5, 1997

Related U.S. Application Data

[63] Continuation of application No. PCT/DK96/00084, Feb. 28, 1996.

[30] Foreign Application Priority Data

Feb. 28, 1995 [DK] Denmark ................................ 0207/95

[51] Int. Cl.$^6$ .................... C07D 261/20; C07D 275/03; C07D 277/02; C07D 307/02; C07D 311/78; C07D 313/20; C07D 337/00; C07D 409/14

[52] U.S. Cl. ................... 540/455; 544/333; 546/270; 548/202; 548/235; 548/241; 548/243; 548/248; 548/267.2; 548/311.7; 548/364.4; 548/518; 549/9; 549/27; 549/60; 549/346; 549/390; 549/472

[58] Field of Search ............................ 540/455; 544/333; 548/202, 235, 241, 243, 248, 267.2, 311.7, 364.4, 518; 549/9, 27, 346, 390, 472, 60; 546/270

[56] References Cited

U.S. PATENT DOCUMENTS

| 4,411,901 | 10/1983 | Temple, Jr. et al. .................... 424/250 |
| 4,452,799 | 6/1984 | Temple, Jr. et al. .................... 424/250 |
| 4,514,414 | 4/1985 | Rondinell et al. ...................... 514/422 |
| 5,143,923 | 9/1992 | Hrib et al. .............................. 514/321 |
| 5,225,412 | 7/1993 | Hrib et al. .............................. 514/254 |

FOREIGN PATENT DOCUMENTS

| 0273 744 A2 | 7/1988 | European Pat. Off. ....... A61K 31/42 |
| 26 02 643 A1 | 7/1977 | Germany .................... A61K 31/425 |
| WO 87/00171 A1 | 1/1987 | WIPO ......................................... 51/4 |

OTHER PUBLICATIONS

Birgitte Sokilde, *Neurotransmitter Defekter I Alzheimers Syge (Design, syntese og biologisk test af heterocykliske muscarine, nicotine og GABA erge receptorligander)*, Danmarks Farmaceutiske Hojskole, Institut for Organisk Kemi, Kobenhavn (Ph.D. Thesis–Date of Publication Unknown).

*Eur.J.Pharmacol.*, vol. 236, (1993), H.S. White et al. "Anticonvulsant Activity of the Gamma–Aminobutyric Acid Uptake Inhibitor N–4, 4–disphenyl–3–butenyl– 4,5,6,7,–tetrahydrioxazolo (4,5–c) pyridin–3–ol" pp. 147–149.

*J.Med Chem.*, vol. 28, 1985, F.E. Ali et al., "Orally Active and Potent Inhibitors of Gamma–Aminobutyric Acid Uptake", pp. 653–660.

*Primary Examiner*—Johann Richter
*Assistant Examiner*—Taofiq A. Solola
*Attorney, Agent, or Firm*—Darby & Darby

[57] ABSTRACT

The present invention relates to novel 4-aminotetrahydrobenzisoxazoles or 4-aminotetrahydrobenziothiazoles having gamma-aminobutanoic acid (GABA)-uptake inhibiting activity and thus useful in the treatment of analgesia, psychosis, convulsions, anxiety, epileptic disorders or muscular and movement disorders, such as spastic disorders or symptoms in Huntington's disease or Parkinson disease.

29 Claims, No Drawings

4-AMINOTETRAHYDROBENZISOXAZOLE OR -ISOTHIAZOLE COMPOUNDS

This is a continuation of international application Ser. No. PCT/DK96/00084, filed Feb. 28, 1996.

The present invention relates to novel 4-aminotetrahydrobenzisoxazoles or -isothiazoles having GABA-uptake inhibiting activity and thus being useful in the treatment of analgesia, psychosis, convulsions, anxiety or muscular and movement disorders, such as spastic disorders or symptoms in Huntington's disease or Parkinsonism. The anticonvulsant activity especially provides usefulness as broad spectrum antiepileptic agents.

BACKGROUND OF THE INVENTION

The neutral amino acid, 4-aminobutanoic acid (GABA), is an inhibitory transmitter in the central nervous system. There is considerable direct and indirect evidence that impaired operation of GABA-mediated inhibitory synapses may be an important causative factor in seizure disorders (P. Krogsgaard-Larsen et al., *Epilepsy Res.* 1987, 1, 77–93) making GABA-ergic drugs potential antiepileptic therapeutic agents.

Furthermore, enhancement of GABA-ergic activity may be useful in the treatment of anxiety, pain, muscular and movement disorders and mental and emotional disorders (W. Löscher, *Eur. J. Pharmacol.*, 1985, 110, 103–108).

While direct stimulation of GABA receptors by agonists does not seem to represent the most suitable therapeutic approach to epileptic diseases (R. G. Fariello et al., Eds., *Neutransmitters, Seizures, and Epilepsy II*, 1984, New York, Raven Press; B. Meldrum and R. Horton, *Eur. J. Pharmacol.* 1980, 61, 231–237; Krogsgaard-Larsen et al., *J. Med. Chem.* 1994, 37, 2489–2505.), GABA neurotransmission may be facilitated by manipulation of the GABA uptake mechanisms. Pharmacological inhibition of the neuronal and/or glial GABA transport, assumed to be responsible for the termination of GABA neurotransmission processes, provides a mechanism for sustaining levels of synaptically released GABA in the synapses and thereby increasing GABA-mediated transmission (P. Krogsgaard-Larsen et al., *J. Med. Chem.* 1994, 37, 2489–2505).

The strategies for such pharmacological interventions may be: 1) effective blockade of both neuronal and glial GABA uptake, or 2) selective blockade of the uptake of GABA into glial cells in order to increase the amount of GABA taken up by the neuronal carrier with subsequent elevation of the GABA concentration in nerve terminals. There is evidence suggesting that glia-selective GABA uptake inhibitors may have particular interest as antiepileptic agents (E. Falch et al., *Drug Design and Delivery*, 1987, 2, 9–21; Falch et al. *Drug Dev. Res.*, 1990, 21, 169–188).

Classical GABA uptake inhibitors are nipecotic acid, guvacine and THPO. Oral active N-substituted derivatives of nipecotic acid and guvacine are described in F. E. Ali et al., *J. Med. Chem.* 1985, 28, 553–560; U.S. Pat. No. 4,383,999 and U.S. Pat. No. 4,514,414 to SmithKline Beckmann Corporation; EP 236342 and EP 231996 to Novo Industri A/S and H. S. White et al., *Eur. J. Pharmacol.* 1993, 236, 147–149.

With regard to convulsion, especially epilepsy, in spite of the fact that antiepileptic drugs are available, many patients fail to experience seizure control. Consequently, it is an object of the present invention to provide new GABA'ergic drugs effective in the treatment of diseases associated with GABA neurotransmission, in particular seizure control.

SUMMARY OF THE INVENTION

It has now been found that a class of novel 4-aminotetrahydrobenzisoxazoles or -isothiazoles inhibits neuronal and/or glial GABA-uptake.

Accordingly, the present invention relates to novel 4-aminotetrahydrobenzisoxazole or -isothiazole compounds having general formula Ia or Ib:

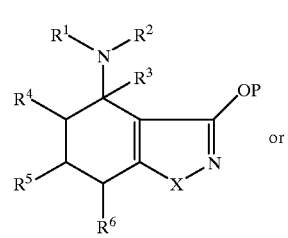

or

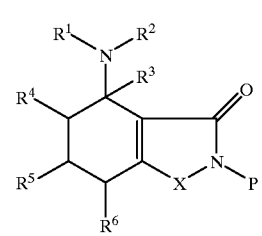

wherein $R^1$ and $R^2$ are independently selected from the group consisting of:

A) hydrogen, cycloalkyl, phenyl, or a group

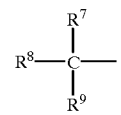

where $R^7$, $R^8$ and $R^9$ are independently selected from the group consisting of hydrogen, lower alkyl, lower alkenyl, lower alkynyl, lower alkoxy-lower alkyl, cycloalkyl, cycloalkyl-lower alkyl, phenyl, phenyl-lower alkyl, phenoxy-lower alkyl and heteroaryl selected from 2-thienyl, 3-thienyl, 2-furyl, 3-furyl, imidazolyl, oxazolyl, pyrazolyl, pyrimidinyl, pyrrolyl, thiazolyl, 1,2,4-triazolyl, 2-pyridyl, 3-pyridyl or 4-pyridyl, any phenyl or heteroaryl group present optionally being substituted with one or two substituents selected from halogen, lower alkyl, lower alkoxy, hydroxy, nitro, lower alkylthio, lower alkylsulfonyl, lower alkyl- or di-(lower)alkylamino, cyano, trifluoromethyl, trifluoromethylthio, trifluoromethylsulfonyloxy and phenyl which again may be substituted with halogen, methyl, methoxy or trifluoromethyl; and any alkyl group present being optionally substituted with one to three hydroxy groups which again are optionally esterified with a $C_{2-18}$ carboxylic acid;

B) a group of general formula Y—$(CH_2)_r$—$(CHR^{11})_s$—$(CH_2)_t$— wherein Y is selected from the following groups (1)–(5):

(1)
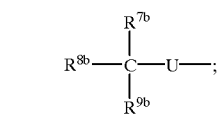

(2)
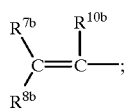

(3)
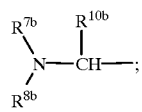

(4)
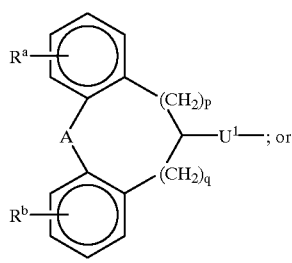

(5)
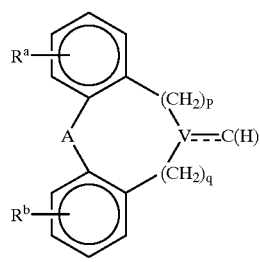

wherein U is $CHR^{10b}$, $NR^{10b}$, O or S, $U^1$ is $NR^{10b}$, O or S; p is 0 or 1; q is 0 or 1;

V is C or N and the dotted line repressents a bond when V is C and no bond when V is N;

A is O, S, $CH_2$, $(CH_2)_2$, $CH=CH-CH_2$, $(CH_2)_3$, $CH=CH$ or $O-CH_2$;

$R^a$ and $R^b$ each represent one or more substituents selected from halogen, lower alkyl, lower alkoxy, hydroxy, nitro, lower alkylthio, lower alkylsulfonyl, lower alkyl- or di(lower alkyl)amino, cyano, trifluoromethyl, trifluoromethylsulfonyloxy and trifluoromethylthio;

r and t are independently 0, 1, 2 or 3, s is 0 or 1, provided that when Y is a group (1) wherein U is $NR^{10b}$, O or S or a group (4), then r+s+t is at least 2;

and when Y is a group (3) or a group (5) where V is N, then r+s+t is at least 1;

$R^{7b}$, $R^{8b}$ and $R^{9b}$ are as defined for $R^7$, $R^8$ and $R^9$ in A) provided that they are not at the same time selected from hydrogen, lower alkyl, lower alkenyl and lower alkynyl;

$R^{10b}$ and $R^{11}$ are independently hydrogen, lower alkyl, lower alkenyl or lower alkynyl; and C) a group of general formula $Y^c-(CH_2)_n-W-(CH_2)_m-$ wherein n is 1, 2 or 3; m is 2 or 3; W is O or S; and $Y^c$ is a group (1)–(5) as defined in B) provided that n may not be 1, when Y is a group (1) or (4) wherein U or $U^1$, respectively, is $NR^{10b}$, S or O;

D) a group of general formula

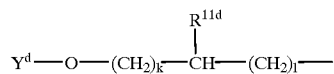

wherein k is 0, 1, 2 or 3;
l is 0, 1, 2 or 3; $R^{11d}$ is as defined for $R^{11}$ in B) above; and
Y is selected from the groups (2) and (5) as defined in B) above and the following groups (6)–(10):

(6)
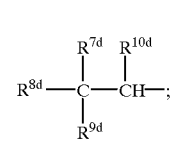

(7)
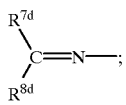

(8)
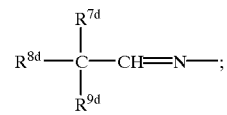

(9)
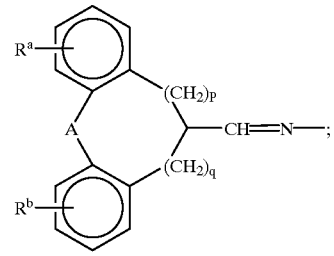

(10)
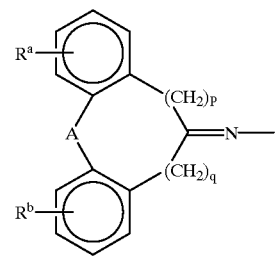

Wherein p, q, $R^a$, $R^b$, and A are as defined in B) and $R^{7d}$–$R^{11d}$ are as defined for $R^{7b}$–$R^{10b}$ and $R^{11}$, respectively, under B) or $R^1$ and $R^2$ together designate alkylene thereby forming a 4–8 membered nitrogen containing ring; or one of $R^1$ and $R^2$ is a group $R^2OCO$ wherein $R^2$ is phenyl, or heteroaryl as defined in A) above or phenyl or such heteroaryl substituted with one or more substituents selected from halogen, lower alkyl, lower alkoxy, hydroxy, nitro, lower alkylthio, lower alkylsulfonyl, lower alkyl- or di(lower)alkylamino, cyano, trifluoromethyl, trifluoromethylthio, trifluoromethylsulfonyloxy, phenyl and phenyl substituted with halogen, methyl, methoxy or trifluoromethyl;

$R^3$–$R^6$ are independently selected from hydrogen, hydroxy and lower alkyl, any alkyl group optionally being substituted with one or two hydroxy groups;

X is oxygen or sulfur;

P is hydrogen or a group ZR wherein

Z is CO, CS, $SO_2$ or $CR'R''$, $R'$ and $R''$ being hydrogen, hydroxy or lower alkyl, and if Z is CO or CS, then R is selected from the groups consisting of:
i) hydrogen, $C_1$–$C_{18}$ alkyl, $C_2$–$C_{18}$ alkenyl, $C_3$–$C_8$ cycloalkyl, $C_3$–$C_8$ cycloalkenyl or $C_4$–$C_{26}$ cycloalk(en)yl-alk(en)yl, optionally substituted with one or two hydroxy groups, or phenyl optionally substituted with one or more substituents selected from the group consisting of halogen, trifluoromethyl, $C_1$–$C_4$ alkyl, $C_1$–$C_4$ alkoxy, $C_1$–$C_4$ alkylthio, $C_1$–$C_5$ acyloxy, or cyano; or
ii) $QR^v$, wherein Q is O or S and $R^v$ is selected from the substituents defined for R under i) above; and
iii) $NR^xR^y$, wherein $R^x$ and $R^y$ independently are selected from the substituents defined for R under i) above or $R^x$ and $R^y$ are combined to form a four to eight membered heterocyclic ring containing from one to three nitrogen atoms and from zero to three oxygen or sulfur atoms; or if Z is $CR'R''$, R is selected from the groups consisting of:
iv) a group $QR^v$ as defined in ii);
v) a group $NR^xR^y$ as defined in iii); or
vi) a group $OC(O)R^z$, $SC(O)R^z$, $OC(S)R^z$ or $SC(S)R^z$ wherein $R^z$ is selected from the substituents defined for R under i) above;

if Z is $SO_2$, R is selected from group i) defined above;

provided that P may not be hydrogen, when $R^1$ to $R^6$ are all hydrogen, X is oxygen and the compound exists as a racemic mixture;

or a pharmaceutically acceptable salt thereof.

The compounds of the invention have been found to inhibit neuronal and/or glial GABA-uptake, some of the compounds predominantly inhibiting the glial uptake. Thus the compounds are useful in the treatment of diseases associated with GABA neurotransmission, e.g. as analgesic, antipsychotic, anticonvulsant, or anxiolytic drugs or as drugs for the treatment of muscular and movement disorders, such as spastic disorders or symptoms of in Huntington's disease or Parkinsonism.

In another aspect the invention provides a pharmaceutical composition comprising at least one novel 4-aminotetrahydrobenzisoxazoles or -isothiazoles of Formula I in a therapeutically effective amount together with a pharmaceutically acceptable carrier and/or diluent.

In a further aspect the present invention provides the use of a 4-aminotetrahydrobenzisoxazoles or -isothiazoles of Formula I for the manufacture of a pharmaceutical preparation for the treatment of the above mentioned disorders and diseases.

Also, the present invention provides a method for the preparation of the 4-aminotetrahydrobenzisoxazoles or -isothiazoles of Formula I.

DETAILED DESCRIPTION OF THE INVENTION

The compounds of general Formula I exist as optical isomers thereof and such optical isomers as well as any mixture thereof, including the racemic mixtures, are also embraced by the invention.

In the present context, the term lower alkyl designates straight or branched $C_{1-4}$ alkyl, such as methyl, ethyl, propyl, isopropyl, butyl and tert.butyl. Similarly, lower alkenyl and lower alkynyl designate such groups having up to 4 carbon atoms and having at least one double or tripple bond, respectively. Lower alkoxy, lower alkylthio, lower alkylsulfonyl, lower alkylamino, lower dialkylamino, etc. similarly designate such groups wherein the alkyl moiety is a lower alkyl group as defined above.

The term cycloalkyl designates a saturated carbocyclic ring having 3–7 carbon atoms, inclusive, and the term halogen designates F, Cl, Br or I.

Alk(en/yn)yl means that the group may be an alkyl, alkenyl or alkynyl group.

Heteroaryl means 2-thienyl, 3-thienyl, 2-furyl, 3-furyl, imidazolyl, oxazolyl, pyrazolyl, pyrimidinyl, pyrrolyl, thiazolyl, 1,2,4-triazolyl, 2-pyridyl, 3-pyridyl or 4-pyridyl.

The compounds wherein P is a group ZR are prodrugs for the compounds wherein P is H. When P is H the compound exists as tautomeric forms as follows:

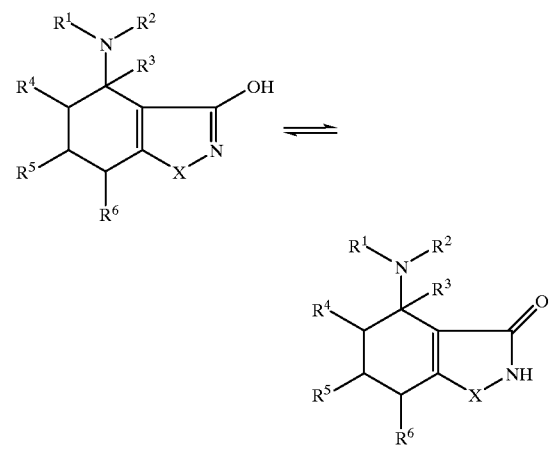

So, when reacted with the proper reactant in order to introduce the group ZR, the said group is either introduced at the O-atom exo to the isoxazole/isothiazole ring or at the ring N-atom depending on the reaction conditions. In the following, compounds wherein P is H, are for the sake of convenience named as having the first mentioned form, i.e. as having formula Ia. Similarly the compounds wherein $R^1$ or $R^2$ is a group $R^2OCO$ are prodrugs for the corresponding compounds wherein $R^1$ or $R^2$ is hydrogen.

The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

It is preferred that $R^1$ is a group as defined in

A) above, namely lower alk(en/yn)yl optionally substituted with hydroxy which may be esterified with a $C_{2-22}$ carboxylic acid, preferably with a $C_{2-4}$ carboxylic acid; or phenyl or phenyl-lower alkyl, optionally substituted with halogen, lower alkyl, lower alkoxy or trifluoromethyl; $R^1$ being more preferably methyl, ethyl or phenylbutyl;

B) above wherein Y is a group of formula (1), (2) or (3), wherein $R^{7b}$ and $R^{8b}$ are phenyl, heteroaryl or substituted phenyl or heteroaryl, most preferably phenyl, phenyl substituted with halogen, lower alkyl, lower alkoxy or trifluoromethyl, 2-thienyl, 2-thienyl substituted with methyl, pyrrolyl or pyrrolyl substituted with methyl or ethyl. In particular Y a group of formula (1) wherein U is $CH_2$ or O or a group of formula (2), or Y is a group of formula (4) or (5), wherein p and q are 0 and A is sulfur or —$CH_2CH_2$— and $R^a$ and $R^b$ are hydrogen.

In formula (1), (2) or (3) $R^{9b}$ is hydrogen is preferably hydrogen or lower alkyl, especially hydrogen and $R^{10b}$ is hydrogen, and in formula (1), (2), (3), (4) and (5) s is preferably 0 and r+t is 0–5, more preferably 1–3, most preferably 2.

C) above where $Y^c$ is a group of formula (1) where U is $CH_2$, a group of formula (2), (3) or (5) in which formulas $R^{7b}$ and $R^{8b}$ are phenyl, heteroaryl or substituted phenyl or heteroaryl, most preferably phenyl, phenyl substituted with halogen, lower alkyl, lower alkoxy or trifluoromethyl, 2-thienyl, 2-thienyl substituted with methyl, pyrrolyl or pyrrolyl substituted with methyl or ethyl. $R^{9b}$ is preferably hydrogen or lower alkyl, especially hydrogen, $R^{10b}$ is hydrogen, and n+m is preferably 0–5, more preferably 1–3, most preferably 2. or D) above where Y is a group of formula (6), (7) or (8), in which formulas $R^{7d}$ and $R^{8d}$ are independently phenyl, phenyl substituted with halogen, lower alkyl, trifluoromethyl or lower alkoxy, in particular chloro, fluoro, methyl, trifluoromethyl, or methoxy, 2-thienyl, 2-thienyl substituted with lower alkyl, most preferably methyl, pyrrolyl or pyrrolyl substituted with methyl or ethyl. $R^{9d}$–$R^{11d}$ are preferably hydrogen and k+l is 0–4, more preferably 0–2, most preferably 1.

$R^2$ is preferably hydrogen, lower alk(en/yn)yl or a group $R^2OCO$. Most preferably $R^2$ is hydrogen or lower alkyl, in particular hydrogen or methyl.

Preferably $R^3$ is hydrogen or lower alkyl, $R^4$–$R^6$ are hydrogen and X is oxygen.

P is preferably hydrogen or a group ZR wherein Z is $CR'R''$, $R'$ and $R''$ being hydrogen, hydroxy or lower alkyl, most preferably hydrogen or methyl, and R is a group $OC(O)R^z$, $SC(O)R^z$, $OC(S)R^z$ or $SC(S)R^z$ wherein $R^z$ is lower alk(en)yl, in particular t-butyl, or optionally substituted phenyl; or wherein Z is CO or CS and R is $NR^xR^y$, wherein $R^x$ and $R^y$ are hydrogen or lower alkyl or $R^x$ and $R^y$ form a heterocyclic ring having one or two N-atoms and being optionally mono- or disubstituted with oxo.

Preferably the compound has the structure of formula Ia.

In particular it is preferred that the group P is different from hydrogen when $R^1$ is a preferred group selected from A) as defined above, especially a lower alk(en/yn)yl group, and $R^2$ is hydrogen or lower alk(en/yn)yl.

When $R^1$ and/or $R^2$ is a group as defined under B), C), or D) it is preferred that P is hydrogen.

In a preferred subclass of the compounds of the invention $R^1$ is a group as defined in A) namely lower alk(en/yn)yl optionally substituted with hydroxy which may be esterified with a $C_{2-22}$ carboxylic acid, or phenyl or phenyl-lower alkyl, optionally substituted with halogen, lower alkyl, lower alkoxy or trifluoromethyl, $R^1$ being most preferably methyl, ethyl or phenylbutyl;

$R^2$ is hydrogen or lower alk(en/yn)yl, in particular hydrogen or methyl;

$R^3$ is hydrogen or lower alkyl, in particular hydrogen or methyl, $R^4$–$R^6$ are hydrogen and X is oxygen;

P is a group ZR wherein Z is $CH_2$ or $CH(CH_3)$, and R is a group $OC(O)R^z$, wherein $R^z$ is lower alkyl or optionally substituted phenyl or heteroaryl; or wherein Z is CO and R is $NR^xR^y$, wherein $R^x$ and $R^y$ are hydrogen or lower alkyl or $R^x$ and $R^y$ form a heterocycle.

In a further preferred subclass of the compounds of the invention $R^1$ is a group as defined in B) above wherein s is 0 and r+t is 0–4, in particular 1–3, and $Y^b$ is a group of formula (1) or (2) wherein $R^{7b}$ and $R^{8b}$ are independently phenyl, phenyl substituted with halogen, lower alkyl, trifluoromethyl or lower alkoxy, in particular chloro, fluoro, methyl, trifluoromethyl, or methoxy, 2-thienyl, 2-thienyl substituted with lower alkyl, most preferably methyl, pyrrolyl or pyrrolyl substituted with methyl or ethyl, $R^{9b}$–$R^{10b}$ are hydrogen and U is $CH_2$ or O or $Y^b$ is a group of formula (5) where p and q are 0 and A is sulfur or —$CH_2CH_2$— and $R^a$ and $R^b$ are hydrogen; and $R^2$, $R^3$, $R^4$–$R^6$ and X are as defined in the preferred subclass above and P is hydrogen.

According to another preferred subclass of the compounds o the invention $R^1$ is a group as defined in C) above where Y is a group of formula (1) where U is $CH_2$, or a group of formula (3) or (5), in which formulas $R^{7b}$ and $R^{8b}$ are independently phenyl, phenyl substituted with halogen, lower alkyl, trifluoromethyl or lower alkoxy, in particular chloro, fluoro, methyl, trifluoromethyl, or methoxy, 2-thienyl, 2-thienyl substituted with lower alkyl, most preferably methyl, pyrrolyl or pyrrolyl substituted with methyl or ethyl, $R^{9b}$ and $R^{10b}$ are hydrogen, W is O, n is 1–3, most preferably 1, and m is 2–4, most preferably 2 or 3; and $R^2$, $R^3$, $R^4$–$R^6$ and X are as defined in the preferred subclass above and P is hydrogen.

According to another preferred subclass of the compounds of the invention $R^1$ is a group as defined in D) above where Y is a group of formula (6), (7) or (8), in which formulas $R^{7d}$ and $R^{8d}$ are independently phenyl, phenyl substituted with halogen, lower alkyl, trifluoromethyl or lower alkoxy, in particular chloro, fluoro, methyl, trifluoromethyl or methoxy, 2-thienyl, 2-thienyl substituted with lower alkyl, most preferably methyl, pyrrolyl, or pyrrolyl substituted with methyl or ethyl, $R^{9d}$, $R^{10d}$ and $R^{11d}$ are hydrogen, W is O, k+l is 0–3, most preferably 1 or 2; and $R^2$, $R^3$, $R^4$–$R^6$ and X are as defined in the preferred subclass above and P is hydrogen.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions methods well known in the art may be used, and any pharmaceutically acceptable carriers, diluents, exipients, or other additive usually used in the art may be used.

Conveniently, the compounds of the invention are administered in unit dosage form containing said compounds in an amount of about 0.1 to 1000 mg.

The total daily dose is usually in the range of about 0.5–5000 mg, and most preferably about 1.0 to 500 mg of the active compound of the invention.

The method of the invention for preparing the novel compounds of formula I comprises:

a) In order to obtain a compound of formula I wherein $R^2$ is hydrogen, removing the acyl protection group of a compound of formula II or III:

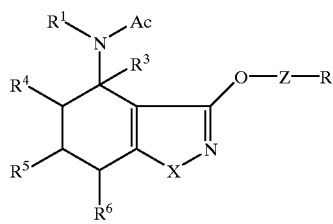

II

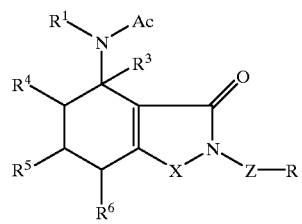

III wherein $R^1$, $R^3$–$R^6$, X and ZR are as defined above and Ac is an acyl protection group;

b) Alkylating an amine of formula $HNR^1R^2$ wherein $R^1$ and $R^2$ are as defined above with a ketone of formula IV or V:

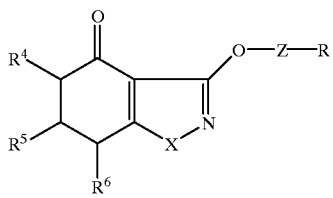

IV

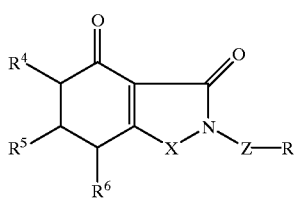

V where $R^4$–$R^6$, X and ZR are as defined above, in the presence of a reducing agent;

c) In order to obtain a compound of formula I wherein P is H, removing the B group of a compound of formula VI or VII:

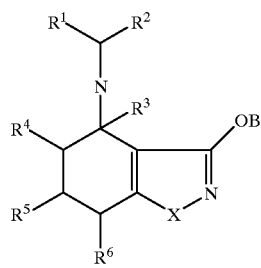

VI

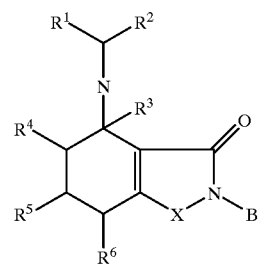

VII wherein $R^1$–$R^6$ and X are as defined above and B is lower alkyl, phenyl lower alkyl or a group ZR as defined above;

d) Reducing the double bond of a Shiff base, oxime, or oxime ether of the following formula VIII or IX:

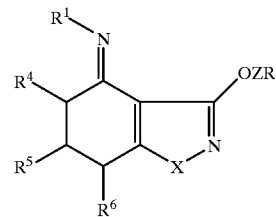

VIII

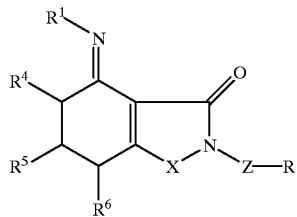

IX wherein $R^1$, $R^4$–$R^6$, X and ZR are as defined above.

e) Arylating a compound of formula X

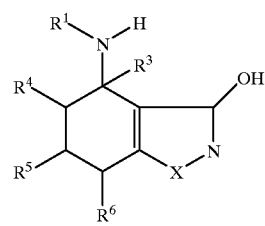

X wherein $R^1$, $R^3$–$R^6$ and X are as defined above with an acylation agent of the formula $R^{2'}$—O—CO-hal, wherein hal is Cl or Br and $R^{2'}$ is as defined above.

The starting material for the preparation of isoxazole intermediates of formulas II to X is 4,5,6,7-tetrahydro-1,2-benzisoxazol-3-ol, which is conveniently prepared according to the method described by R. Jaquier et al., Bull.Soc.Chim.Fr.1970, 5, 1978–1985. Starting material for the corresponding thioisoxazoles is cyclohexanone-2-carboxamide. Details for the conversion of these intermediates to compounds of formula I are given in the Experimental Section.

The acyl protection group in method a) is conveniently removed by aqueous hydrolysis catalyzed by bases (sodium or potassium hydroxide or potassium carbonate) or acids (hydrochloric or hydrobromic), hydrogenation of benzyloxy-carbonyl or 1,1,1-trichloroethyloxycarbonyl groups, or anhydrous acid catalyzed deprotection of e.g. the t-Boc protection group. Hydrogenation either involves catalytic hydrogenation in a Parr apparatus, using Pd as catalyst, or hydrogenation in presence of metals such as zinc in aqueous acidic solution such as diluted acetic acid.

Amines used in the reductive alkylation in method b) are commercially available or prepared according to well established literature methods for example as described in F. E. Ali et al., *J. Med. Chem.* 1985, 28, 553–560; U.S. Pat. No. 4,383,999 and U.S. Pat. No. 4,514,414 to SmithKline Beckmann Corporation; EP 236342 and EP 231996 to Novo Industri A/S and H. S. White et al., *Eur. J. Pharmacol.* 1993, 236, 147–149. $NaBH_4$ or $NaCNBH_3$, preferably in the presence of a dehydrating agent such as a molecular sieve, may be used as reducing agent in a protic solvent such as methanol, ethanol, water or mixtures thereof. Proper salts of the amines are used to obtain optimal pH conditions.

The protecting groups B in method c) are effectively removed by base or acid catalyzed hydrolysis. If B is an O-alkyl group such as methoxy or ethoxy it might be conveniently removed by treatment with strong acid (e.g. 48% hydrobromic acid in glacial acetic acid) at elevated temperatures.

Schiff bases, oximes, or oxime ethers in method d) are conveniently reduced to the corresponding amine derivatives by catalytic hydrogenation using e.g. Pd or Pt as catalysts, or by reduction with amalgamated aluminum or with $LiAlH_4$ or $AlH_3$.

EXPERIMENTAL SECTION

Melting points were determined on a Buchi SMP-20 apparatus and are uncorrected. Mass spectra were obtained on a Quattro MS-MS system from VG Biotech, Fisons Instruments. The MS-MS system was connected to an HP 1050 modular HPLC system. A volume of 20–50 $\mu$l of the sample (10 $\mu$g/ml) dissolved in a mixture of 1% acetic acid in acetonitril/water 1:1 was introduced via the autosampler at a flow of 30 $\mu$l/min into the Electrospray Source. Spectra were obtained at two standard sets of operating conditions. One set to obtain molecular weight information (MH+) (21 eV) and the other set to induce fragmentation patterns (70 eV). The background was subtracted. The relative intensities of the ions are obtained from the fragmentation pattern. When no intensity is indicated for the Molecular Ion (MH+) this ion was only present under the first set of operating conditions. $^1$H NMR spectra were recorded of all novel compounds at 250 MHz on a Bruker AC 250 spectrometer, at 200 MHz on a Bruker AC 200 F. spectrometer, or as otherwise stated in the experiments. Deuterated chloroform (99,8% D) or dimethyisulfoxide (99,9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui= quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230–400 mesh ASTM was used.

EXAMPLE 1

3-Ethoxy-4,5,6,7-tetrahydro-1,2-benzisoxazole, 1a

The starting material 4,5,6,7-tetrahydro-1,2-benzisoxazol-3-ol was prepared according to a literature procedure (R.Jaquier et al., *Bull.Soc.Chim.Fr.* 1970, 5, 1978–1985). To a solution of this isoxazole derivative (100 g) in acetone (3 L) was added potassium carbonate (200 g). After heating at 50° C. for 45 minutes a solution of bromoethane (170 mL) in acetone (300 mL) was added dropwise during 1.5 hours. The mixture was stirred overnight at 50° C. After cooling, inorganic salts were filtered off and acetone evaporated in vacuo. The remaining mixture of O- and N-alkylated product was separated by column chromatography on silica gel (eluted with ethyl acetate/heptane 40:60). Evaporation of the solvents afforded 65 g of the title product as a viscous oil. $^1$H NMR ($CDCl_3$): δ1.40 (t, 3H), 1.70–1.85 (m, 4H), 2.25–2.30 (m, 2H), 2.50–2.60 (m, 2H), 4.30 (q, 2H).

EXAMPLE 2

3-Ethoxy-4,5,6,7-tetrahydro-1,2-benzisoxazol-4-one, 2a (Method d))

To a solution of 3-ethoxy-4,5,6,7-tetrahydro-1,2-benzisoxazole 1a (35 g) in glacial acetic acid (500 mL) at 10° C. was added concentrated $H_2SO_4$ (29 mL). A solution of sodium dichromate (71 g) in glacial acetic acid (300 mL) kept at 40–45° C. was added dropwise during one hour at 20–25° C. The mixture was stirred for another 3 hours at 25–30° C. The reaction mixture was poured onto ice and diethyl ether (3 L). pH was adjusted to >10 by addition of concentrated aqueous NaOH. The organic phase was separated and worked up. The remaining crude title compound was purified by column chromatography on silica gel (eluted with ethyl acetate/heptane 1:1). Pure 3-ethoxy-4,5,6,7-tetrahydro-1,2-benzisoxazol-4-one was washed with diisopropyl ether and dried. Yield 27 g. Mp 98–99° C.

EXAMPLE 3

(R,S)-4-amino-3-ethoxy-4,5,6,7-tetrahydro-1,2-benzisoxazole, 3a

To a solution of 3-ethoxy-4,5,6,7-tetrahydro-1,2-benzisoxazol-4-one 2a (8 g) in ethanol (400 mL) were added hydroxylammonium hydrochloride (20 g), $Na_2CO_3$ (16 g), and water (600 mL). The mixture was heated at reflux temperature for 3 hours. The solvents were partly evaporated (2/3). The remaining mixture was left at room temperature for 0.5 hours and the precipitated crystalline product was finally filtered off, washed with water and dried. Yield of the oxime derivative 7 g. Mp 216–218° C. To a solution of $HgCl_2$ (200 g) in water (4 L) was added aluminium foil (125 g) cut into small pieces (0.5×0.5 cm). These pieces were left for about 1 minute and subsequently filtered off and washed with ethanol. The oxime derivative (25 g) was suspended in methanol (2 L) and water (500 mL) and the aluminium foil was added. The resulting mixture was stirred for 5 days. The precipitates were filtered off and washed with methanol. The combined methanol solutions were evaporated in vacuo. The remaining crude product was stirred with diethyl ether. Undissolved starting material (oxime) was filtered off and the diethyl ether was evaporated in vacuo leaving the title compound as a viscous oil. Yield 23 g. $^1$H NMR ($CDCl_3$) δ1.40 (t, 3H), 1.40–1.1.75 (m, 4H), 1.90–2.05 (m, 2H), 2.50–2.60 (m, 2H), 3.90 (broad t, 1H), 4.30 (q, 2H).

EXAMPLE 4

4-amino-3-hydroxy-4,5,6,7-tetrahydro-1,2-benzisoxazole, hydrobromide 4a enantiomer A (R,S)-4-Amino-3-ethoxy-4,5,6,7-tetrahydro-1,2-benzisoxazole 3a (17.5 g) was dissolved in dichloromethane (500 mL) and triethylamine (30 mL) was added at 5° C. A solution of (R)-(-)-α-methoxyphenylacetyl chloride (22 g) in dichloromethane (80 mL) was added dropwise at 5–10° C. The resulting mixture was stirred for 2 hours at room temperature. Water (2 L) was added and the organic phase was separated, washed with diluted hydrochloric acid and worked up as above. Yield 34 g. The diastereomers of this mixture were separated by preperative HPLC on silica gel (eluted with heptane/ethyl acetate 3:2). Yield of the less polar diastereomer B 13 g as an oil. Yield of the more polar diastereomer A 11.5 g. Mp 96–97° C. $^1$H NMR (CDCl$_3$) δ1.30 (t, 3H), 1.80–2.05 (m, 4H), 2.45–2.75 (m, 2H), 3.30 (s, 3H), 4.25 (q, 2H). 4.60 (s, 1H), 4.95 (dt, 1H), 6.85 (broad d, 1H), 7.30–7.45 (m, 5H). The diastereomer A (3.7 g) was dissolved in 48% aqueous hydrobromic acid (175 mL) and water (175 mL). This solution was refluxed for 1.25 hours. The solvent was evaporated in vacuo. Dichloromethane and water were added. The organic phase was separated, washed with water and finally discarded. The combined aqueous phases were evaporated in vacuo. Ethanol/ether 1:1 were added, the precipitates were filtered off, and the solvents evaporated leaving the impure crude hydrobromide salt 4a (enantiomer A) as an oil. Yield 4.0 g. Purification is shown below in Examples 5 and 6.

The crude hydrobromic salt of enantiomer B, 4b was isolated correspondingly from diastereomer B.

EXAMPLE 5

4-(tert-butyloxycarbonylamino)-3-hydroxy-4,5,6,7-tetrahydro-1,2-benzisoxazole 5a enantiomer A A mixture of crude 4-amino-3-hydroxy-4,5,6,7-tetrahydro-1,2-benzisoxazole, hydrobromide 4a, enantiomer A from Example 4 (4.0 g) was dissolved in a 1:1 mixture of water/dioxane. After cooling to 10° C., a solution of NaOH (1.2 g in 12 mL of water) was added. Di-tert-butyl dicarbonate (3.5 g) dissolved in dioxane (12 mL) was added at 15–20° C. The mixture was stirred at room temperature for 1.5 hours. Water (120 mL) was added and pH was adjusted >10 by adding a small amount of NaOH. After stirring for additionally 30 minutes, diethyl ether (200 mL) was added. The organic phase was separated and discarded. By addition of KHSO$_4$ pH was adjusted to 3–4 and the aqueous phase was extracted with diethyl ether (2×100 mL). The combined organic phases were worked up as above leaving the crude Boc-protected title compound. The pure title compound 5a was obtained by column chromatography on silica gel (eluted with heptane/ethyl acetate/ethanol 7:3:1 Yield 0.9 g. Mp: 135° C. $^1$H NMR (CDCl$_3$) δ1.45 (s, 9H), 1.75–2.10 (m, 4H), 2.45–2.70 (m, 2H), 4.50 (dt, 1H), 5.05 (broad d, 1H).

The corresponding enantiomer B was prepared in a similar way:

4-(tert-butyloxycarbonylamino)-3-hydroxy-4,5,6,7-tetrahydro-1,2-benzisoxazole, 5b enantiomer B. Mp 134° C. The NMR spectrum was identical to the spectrum above for compound 5a.

EXAMPLE 6

(+)-4-amino-3-hydroxy-4,5,6,7-tetrahydro-1,2-benzisoxazole, hydrochloride 6a (=(s)-isomer The boc-protected enantiomer A, 5a (0.9 g) obtained in Example 5 was dissolved in a saturated solution of HCl in ether (200 mL) and stirred at room-temperature for 1.25 hours. The solvent was evaporated and the remaining oil was dissolved in a 1:1 mixture of ethanol in ether. The precipitated crystalline title compound was filtered off. Yield: 0.5 g. Mp 209–210° C. [α]$_D$=+19.40° (c=1.0 M, methanol). $^1$H NMR (DMSO-d$_6$) δ1.75–2.05 (m, 4H), 2.55–2.65 (m, 2H), 4.25 (broad t, 1H), 8.40 (broad s, 4H). MS m/z (%): 155 (MH+, 49%), 138 (100%), 113 (16%), 65 (58%).

The (-)-isomer (or (R-)-isomer) was prepared in a corresponding way:

(-)-(R)-4-amino-3-hydroxy-4,5,6,7-tetrahydro-1,2-benzisoxazole, hydrochloride 6b. Mp 209–210° C. [α]$_D$=-20.0° (c=1.0 M, methanol). $^1$H NMR and MS spectra were the same as for the (+)-enantiomer above.

Compound 8a was resolved in a correponding way via HPLC separation of the diastereomeric (R)-(-)-α-methoxyphenylacyl carboxamide derivatives of compound 7a. A modification of the method in Example 4 was used to splitt off protecting groups.

(+)-3-hydroxy-4-methylamino-4,5,6,7-tetrahydro-1,2-benzisoxazole, hydrobromide 6c To the most polar diastereomer (9 g) separated via HPLC chromatography was dissolved in dry THF a solution of 1M lithiumtriethylborhydride in dry THF (80 mL) was added dropwise during 20 minutes at 0–5° C. The mixture was further stirred overnight at roomtemperature. The mixture was poured onto ice (500 g) and pH was adjusted to 2 by addition of concentrated hydrochloric acid. To remove THF the mixture was evaporated in vacuo. To the remaining aqueous solution was extracted twice with ethyl acetate (50 mL). The remaining aqueous solution was made alkaline by addition of concentrated NaOH solution (pH=11). Ethyl acetate (100 mL) was added and the organic phase was subsequently separated and worked up as above. All of the thus isolated 3-ethoxy-4-methylamino-4,5,6,7-tetrahydro-1,2-benzisoxazole enantiomer (4.6 g) was dissolved in a mixture of 33% Hbr in glacial acetic acid (150 mL). The mixture was heated to 90° C. and stirred for an hour. The solution was evaporated in vacuo. The remaining visceous oil was stirred with a mixture of ethanol/diethyl ether 1:1. The precipitated hydrobromic acid salt was filtered off and dried overnight in vacuo. Yield 4.2 g. Mp 207–209° C. [α]$_D$=+5.6° (c=1.0 M, methanol). $^1$H NMR and MS spectra were identical to spectra of the racemic mixture, compound 8a. Enantiomeric purity by HPLC determination : ee >99.

(-)-3-hydroxy-4-methylamino-4,5,6,7-tetrahydro-1,2-benzisoxazole, hydrobromide 6d was prepared analogously from the other diastereomeric carboxamide derivative. Mp 208–209° C. [α]$_D$=-5.9° (c=1.0 M, methanol). Enantiomeric purity by HPLC determination: ee >99.

EXAMPLE 7

(R,S)-3-Ethoxy-4-methylamino-4,5,6,7-tetrahydro-1,2-benzisoxazole 7a

To a solution of 3-ethoxy-4,5,6,7-tetrahydro-1,2-benzisoxazol-4-one 2a (4.5 g) in methanol (100 mL) were added methylamine hydrochloride (15 g), a 33% solution of methylamine (5 mL) in ethanol, and molecular sieves (3 Å) powder. Finally sodium cyanoborohydride was added (7 g). The mixture was stirred overnight. Inorganic salts were filtered off and the solvents evaporated in vacuo. Ethyl acetate and water were added and pH was adjusted >10 by addition of concentrated NaOH solution. The organic phase was subsequently worked up as above. The crude title compound was used without further purification. Yield 4.8 g. $^1$H NMR (CDCl$_3$) δ1.40 (t, 3H), 1.65–1.80 (m, 3H), 1.85–2.00 (m, 1H), 2.05 (s, 1H), 2.45 (s, 3H), 2.50–2.60 (m, 2H), 3.60 (t, 1H), 4.30 (q, 2H).

The following 3-ethoxyisoxazoles were synthesized in a similar way:

(R,S)-4-[4,4-Bis(4-fluorophenyl)butan-1-ylamino]-3-ethoxy-4,5,6,7-tetrahydro-1,2-benzisoxazole 7b. $^1$H NMR (CDCl$_3$) δ1.35 (t, 3H), 1.40–1.55 (m, 3H), 1.60–1.85 (m, 3H), 1.90–2.10 (m, 3H), 2.45–2.60 (m,2H), 2.65 (t, 2H), 3.70 (t, 1H), 3.85 (t, 1H), 4.30 (q, 2H), 6.95 (t, 4H), 7.15 (dd, 4H).

(R,S)-3-Ethoxy-4-(2-hydroxyethylamino)-4,5,6,7-tetrahydro-1,2-benzisoxazole 7c Mp 72–74° C. $^1$H NMR (CDCl$_3$) δ1.40 (t, 3H), 1.65–2.00 (m, 4H), 2.45 (s, 2H), 2.45–2.70 (m, 2H), 2.85 (t, 2H), 3.60–3.70 (m, 2H), 3.75 (t, 1H), 4.30 (q, 2H)

(R,S)-3-Ethoxy-4-(1-pyrrolidinyl)-4,5,6,7-tetrahydro-1,2-benzisoxazole 7d $^1$H NMR (CDCl$_3$) δ1.40 (t, 3H), 1.40–1.55 (m, 2H), 1.70–1.90 (m, 6H), 2.00–2.25 (m, 2H), 2.50–2.80 (m, 4H), 3.25 (t, 1H), 4.30 (dq, 2H).

(R,S)-4-(4,4-diphenylbutan-1-ylamino)-3-ethoxy-4,5,6,7-tetrahydro-1,2-benzisoxazole, 7e. Prepared via the butylamine 30a and isolated as an oil. $^1$H NMR (CDCl$_3$) δ1.35 (t, 3H), 1.40–1.50 (m, 2H), 1.60 (s, 1H), 1.60–2.00 (m, 6H), 2.00–2.20 (m, 2H), 2.45–2.60 (m, 2H), 2.65 (t, 2H), 3.65 (t, 1H), 3.85 (t, 1H), 4.30 (q, 2H), 7.10–7.30 (m, 10H).

(R,S)-4-(4-phenylbutan-1-ylamino)-3-ethoxy-4,5,6,7-tetrahydro-1,2-benzisoxazole7f. Isolated as an oil. $^1$H NMR (CDCl$_3$) δ1.40 (t, 3H), 1.60 (s, 1H), 1.50–2.00 (m, 8H), 2.50–2.70 (m, 6H), 3.70 (t, 1H), 4.30 (q, 2H), 7.15–7.35 (m, 5H).

(R,S)-4-(3,3-diphenylpropan-1-ylamino)-3-ethoxy-4,5,6,7-tetrahydro-1,2-benzisoxazole 7g. Isolated as an oil. $^1$H NMR (CDCl$_3$) δ1.40 (t, 3H), 1.60 (s, 1H), 1.60–1.80 (m, 4H), 1.85–2.00 (m, 1H), 2.25 (q, 2H), 2.50–2.65 (m, 3H), 3.65 (t, 1H), 4.10 (t, 1H), 4.25 (q, 2H), 7.15–7.35 (m, 10H).

(R,S)-4-[N-[3-(10,11-dihydrodibenzo[a,d]cyclohept-5-ylidene)propane-1-yl]amino]-3-ethoxy-4,5,6,7-tetrahydro-1,2-benzisoxazole, 7h. Prepared via the 3-(10,11-dihydrodibenzo[a,d]cyclohept-5-ylidene)propylamine, hydrochloride (prepared as described in J. Org. Chem. (1962), Vol. 27, 4134–37) and isolated as an oil. $^1$H NMR (CDCl$_3$) δ1.40 (t,3H), 1.50–2.05 (m,6H), 2.35 (q,2H), 2.40–2.65 (m,2H), 2.65–2.85 (m,2H), 2.85–3.50 (m,3H), 3.65 (t,1H), 4.25 (q,2H), 5.90 (t,1H), 7.00–7.07 (m,1 H), 7.07–7.21 (m,6H), 7.21–7.33 (m,1H).

EXAMPLE 8A (R,S)-3-Hydroxy-4-methylamino-4,5,6,7-tetrahydro-1,2-benzisoxazole, hydrobromide 8a (Method c)

A solution of (R,S)-3-Ethoxy-4-methylamino-4,5,6,7-tetrahydro-1,2-benzisoxazole 7a (3.8 g) in a 33% solution of HBr in glacial acetic acid (150 mL) was heated at 60–75° C. for one hour. The solvents were evaporated in vacuo and a 1:1 mixture of ethanol/ether was added. The crystalline hydrobromic salt 8a was filtered off. Yield: 3.6 g. Mp: 184–186° C. $^1$H NMR (DMSO-d$_6$) δ1.75–2.15 (m, 4H), 2.65 (s, 3H), 2.60–2.70 (m, 2H), 4.20 (broad signal, 1H), 8.60 (broad s, 1H).

The following compounds were synthesized correspondingly:

(R,S)-4-[4,4-Bis(4-fluorophenyl)butan-1-ylamino]-3-hydroxy-4,5,6,7-tetrahydro-1,2-benzisoxazole, hydrobromide 8b Mp 205–206° C. $^1$H NMR (DMSO-d$_6$) δ1.45–1.60 (m, 2H), 1.70–2.10 (m, 6H), 2.55–2.70 (m, 2H), 3.05 (t, 2H), 4.00 (t, 1H), 4.20 (broad s, 1H), 7.15 (t, 4H), 7.35 (dd, 4H). MS m/z (%): 399 (MH+, 4%), 138 (100%), 67 (84%).

(R,S)-4-(2-Acetyloxyethylamino)-3-hydroxy-4,5,6,7-tetrahydro-1,2-benzisoxazole, hydrobromide 8c. Mp 164–165° C. $^1$H NMR (DMSO-d$_6$) δ1.75–1.95 (m, 2H), 2.00–2.20 (m, 2H), 2.10 (s, 3H), 2.55–2.70 (m, 2H), 3.30 (t, 2H), 4.20–4.40 (m, 3H). MS m/z (%): 241 (MH+, 17%), 138(59%), 67 (100%), 41 (84%).

(R,S)-3-Hydroxy-4-(1-pyrrolidinyl)-4,5,6,7-tetrahydro-1,2-benzisoxazole, hydrobromide 8d Mp 209–210° C. $^1$H NMR (DMSO-d$_6$) δ1.70–2.30 (m, 8H), 2.60–2.75 (m, 2H), 3.10–3.70 (m, 4H), 4.35 (broad s, 1H) MS m/z (%): 209 (MH+, 5%), 138 (35%), 72 (56%), 67 (100%), 41 (79%).

(R,S)-4-(2-propen-1-ylamino)-3-hydroxy-4,5,6,7-tetrahydro-1,2-benzisoxazole, oxalate (acetone) 8f. This compound was purified via the 4-tert.-butyloxycarbonylamino derivative, which was deprotected as described in Example 8B. Mp 182–183° C. $^1$H NMR (DMSO-d$_6$) δ1.75–2.20 (m, 4H), 2.60–2.75 (m, 2H), 3.65 (d, 2H), 4.15 (broad s, 1H), 5.40 (d, 1H), 5.45 (d, 1H), 5.85–6.00 (m, 1H), 7.70 (broad signal, 3H). MS m/z (%): 195 (MH+, 9%), 138 (57%), 67 (100%), 41 (92%).

(R,S)-4-(4,4-diphenylbutan-1-ylamino)-3-hydroxy-4,5,6,7-tetrahydro-1,2-benzisoxazole, hydrobromide 8g. Mp 221–222° C. (ethanol). $^1$H NMR (DMSO-d$_6$) δ1.45–1.65 (m, 2H), 1.70–2.10 (m, 6H), 2.55–2.75 (m, 2H), 3.05 (t, 2H), 3.95 (t, 1H), 4.20 (broad s, 1H), 7.15–7.40 (m, 10H). MS m/z (%): 363 (MH+, 100%), 138 (89%).

(R,S)-4-(4-phenylbut-1-ylamino)-3-hydroxy-4,5,6,7-tetrahydro-1,2-benzisoxazole, hydrobromide 8h. Mp 202–204° C. (ethanol). $^1$H NMR (DMSO-d$_6$) δ1.55–1.65 (m, 4H), 1.70–2.15 (m, 4H), 2.50–2.70 (m, 4H), 3.00 (broad t, 2H), 4.25 (broad s, 1H), 7.15–7.35 (m, 5H). MS m/z (%): 287 (MH+, 6%), 138 (100%), 91 (42%), 67 (63%).

(R,S)-4-(3,3-diphenylpropan-1-ylamino)-3-hydroxy-4,5,6,7-tetrahydro-1,2-benzisoxazole, hydrobromide 8i. Mp 218–220° C. (ethanol). $^1$H NMR (DMSO-d$_6$) δ1.70–2.10 (m, 4H), 2.40 (t, 2H), 2.55–2.70 (m, 2H), 2.95 (t, 2H), 4.05 (t, 1H), 4.25 board s, 1H), 7.15–7.40 (m. 10H). MS m/z (%): 349 (MH+, 5%), 138 (100%), 67 (30%).

The following compounds were prepared in a similar manner exept that the title compounds were crystallized from acetone (8j, 8k, 8l, 8m, 8n, 8p) or diethyl ether (8o).

(R,S)-4-[N-[3-(10,11-dihydrodibenzo[a,d]cyclohept-5-ylidene)propane-1-yl]amino]-3-hydroxy-4,5,6,7-tetrahydro-1,2-benzisoxazole, hydrobromide, 8j. Mp 228–230° C. (dec.). $^1$H NMR (DMSO-d$_6$) δ1.55–2.00 (m,4H), 2.15–2.65 (m,4H), 2.65–3.00 (m,4H), 3.10–3.40 (m,2H), 3.77–3.87 (m,1H), 5.80 (t,1H), 7.00–7.28 (m,8H), MS m/z (%): 387 (MH+, 5%), 233 (7%), 138 (41%), 43 (100%)

(R,S)-4-[N-[3-(10,11-dihydrodibenzo[a,d]cyclohept-5-ylidene)propane-1-yl]methylamino]-3-hydroxy-4,5,6,7-tetrahydro-1,2-benzisoxazole, hydrobromide, 8k. Mp 215–217° C. (dec.). $^1$H NMR (DMSO-d$_6$) δ1.70–2.10 (m,4H), 2.40–2.95 (m,6H), 3.05–3.44 (m,7H), 4.34–4.43 (m,1H), 5.80 (t,1H), 7.05–7.30 (m,8H), MS m/z (%): 401 (MH+, 26%), 265 (66%), 233 (30%), 138 (84%), 43 (100%)

(R,S)-4-[N-3-(Phenothiazin-10-yl)propane-1-yl]amino]-3-hydroxy-4,5,6,7-tetrahydro-1,2-benzisoxazole, hydrobromide, 8l. Mp 187–189° C. $^1$H NMR (DMSO-d$_6$) δ1.65–2.12 (m,6H), 2.50–2.71 (m,2H), 3.00–3.16 (m,2H), 3.95 (t,2H), 4.09–4.20 (m,1H), 6.97 (dd,2H), 7.07 (d,2H), 7.10–7.26 (m,4H), MS m/z (%): 394 (MH+, 3%), 256 (7%), 138 (18%), 43 (100%)

(R,S)-4-[N-[4,4-Di-(2-tolyl)butan-1-yl]-methylamino]-3-hydroxy-4,5,6,7-tetrahydro-1,2-benzisoxazole, hydrobromide, 8m. Mp 193–195° C. (dec.). $^1$H NMR (DMSO-d$_6$) δ1.65–2.20 (m,8H), 2.26 (s,6H), 2.55–2.80 (m,5H), 3.15–3.35 (m,2H), 4.25 (t, 1H), 4.36–4.47 (m,1H), 7.03–7.21 (m,8H), MS m/z (%): 405 (MH+, 4%), 268 (27%), 138 (30%), 43 (100%)

(R,S)-4-[N-[4,4-Di-(2-tolyl)butan-1-yl]amino]-3-hydroxy-4,5,6,7-tetrahydro-1,2-benzisoxazole, hydrobromide, 8n. Mp 217–219° C. (dec.). $^1$H NMR (DMSO-d$_6$) δ1.55–2.18 (m,8H), 2.25 (d,6H), 2.52–2.75 (m,2H), 3.06 (t,2H), 4.13–4.27 (m,2H), 7.03–7.20 (m,8H), MS m/z (%): 391 (MH+, 7%), 195 (15%), 145 (80%), 138 (92%), 105 (100%)

(R,S)-4-[N-[1,1-Di-(2-tolyl)but-1-en-4-yl]methylamino]-3-hydroxy-4,5,6,7-tetrahydro-1,2-benzisoxazole, 8o. Mp 177–179° C. $^1$H NMR (DMSO-d$_6$) δ1.70–2.14 (m,8H), 2.21 (s,3H), 2.36–2.80 (m,6H), 3.15–3.40 (m,2H), 4.35–4.47 (m,1H), 5.74 (t, 1H), 6.98–7.30 (m,8H), MS m/z (%): 403 (MH+, 19%), 266 (40%), 143 (77%), 138 (100%), 105 (49%), 67 (20%)

(R,S)-4-[N-1,1-Di-(2-tolyl)but-1-en-4-yl]amino]-3-hydroxy-4,5,6,7-tetrahydro-1,2-benzisoxazole, hydrobromide, 8p. Mp 209–211° C. (dec.). $^1$H NMR (DMSO-d$_6$) δ1.70–2.15 (m,7H), 2.22 (s,3H), 2.27–2.45 (m,2H), 2.54–2.73 (m,2H), 3.11 (t,2H), 4.16–4.24 (m,1H), 5.73 (t,1H), 6.96–7.26 (m,8H), MS m/z (%): 389 (MH+, 5%), 143 (33%), 138 (100%), 105 (29%), 67 (44%).

EXAMPLE 8B (R,S)-3-Hydroxy-4-methylamino-4,5,6,7-tetrahydro-1,2-benzisoxazole, hydrobromide, 8a (Method c))

This method is an alternative way to the method in Example 8A of preparing compound 8a and similar derivatives.

A solution of di-tert-butyl dicarbonate (3.56 g) in THF (50 mL) was added to a solution of (R,S)-3-ethoxy-4-amino-4,5,6,7-tetrahydro-1,2-benzisoxazole, hydrobromide 3a (2.60 g) and potassium carbonate (2.07 g) in water (25 mL). The mixture was stirred at room temperature for 20 h and evaporated. Water (30 mL) was added to the residue and the mixture was extracted with ether (3×50 mL). The combined organic extracts were dried and evaporated, and the residue was recrystallized from ether/light petroleum to give (R,S)-3-ethoxy-4-(tert.butyloxycarbonylamino)-4,5,6,7-tetrahydro-1,2-benzisoxazole (2.69 g): mp 111–113° C. 60% Sodium hydride in mineral oil (425 mg) was added in small portions to a solution of the said compound (1.00 g) and methyl iodide (2.18 mL) in THF (45 mL). The mixture was stirred overnight at room temperature and methanol was added to destroy excess of sodium hydride. After evaporation, water (25 mL) was added to the residue. Extraction with ethyl acetate (3×50 mL), drying and evaporation gave (R,S)-3ethoxy-4-(N-methyl-tert.butyloxycarbonylamino)-4,5,6,7-tetrahydro-1,2-benzisoxazole (1.05 g) as a yellow oil. $^1$H NMR (60 MHz, CDCl$_3$) δ1.40 (t, 3H), 1.55 (s, 9H), 1.65–2.2 (m, 4H), 2.55 (m, 2H), 2.60 (s, 3H), 4.35 (q, 2H), 5.20 (m, 1 H). A 33% solution of hydrobromic acid in glacial acetic acid (15 mL) was added to (R,S)-3-ethoxy-4-(N-methyl-tert-butyloxycarbonylamino)-4,5,6,7-tetrahydro-1,2-benzisoxazole (1.05 g) and the mixture was stirred at 80° C. for 25 min. After evaporation, 33% hydrobromic acid in glacial acetic acid (15 ml) was added to the residue and the mixture was stirred at 80° C. for 25 min. Evaporation and recrystallization of the residue (acetonitrile-ethanol-ether) gave the title compound (807 mg): mp 188–190° C. $^1$H NMR (60 MHz, D$_2$O) δ2.05 (m, 4H), 2.75 (m, 2H), 2.85 (s, 3H), 4.35 (m, 1 H).

The following compound was prepared in a similar manner by using ethyl iodide in stead of methyl iodide:

(R,S)-4-Ethylamino-3-hydroxy-4,5,6,7-tetrahydro-1,2-benzisoxazole, hydrobromide 8e Mp: 188–191° C. (from acetonitrile-ethanol-ether). $^1$H NMR (60 MHz, D$_2$O) δ1.30 (t, 3H), 2.05 (m, 4H), 2.70 (m, 2H), 3.25 (q, 2H), 4.35 (m, 1 H).

EXAMPLE 9

(R,S)-4-(2-Hydroxyethylamino)-3-hydroxy-4,5,6,7-tetrahydro-1,2-benzisoxazole, hydrobromide 9a To a solution of (R,S)-4-(2-acetyloxyethylamino)-3-hydroxy-4,5,6,7-tetrahydro-1,2-benzisoxazole, hydrobromide 8c (1.3 g) in water (50 mL) was added 48% aqueous HBr (7 mL). The mixture was heated at 100° C. for an hour. The solvent was evaporated in vacuo and the remaining oil was dissolved in ethanol. Upon evaporation of a major fraction of the ethanol, the hydrobromide salt of compound 9a crystallized and was subsequently filtered off and dried. Yield: 0.9 g. Mp 172–173° C. $^1$H NMR (DMSO-d$_6$) δ1.70–1.95 (m, 2H), 1.95–2.30 (m, 2H),2.55–2.75 (m, 2H), 3.10 (t, 2H), 3.70 (q, 2H), 4.25 (broad s, 1H), 5.20 (broad s, 1H), 8.65 (broad s, 2H), 11.95 (broad s, 1H). MS m/z (%): 199 (MH+, 16%), 138 (33%), 67 (91%), 41 (100%).

EXAMPLE 10

(R,S)-4-[N-[4,4-Bis(4-fluorophenyl)butan-1-yl]-N-methylamino]-3-ethoxy-4,5,6,7-tetrahydro-1,2-benzisoxazole 10a To (R,S)-3-ethoxy-4-methylamino-4,5,6,7-tetrahydro-1,2-benzisoxazole 7a (1.0 g) in methyl isobutyl ketone (MIBK) (10 mL) were added bis-4,4-(4-fluorophenyl)-1-butylchloride (2.0 g), potassium carbonate (1.0 g), and potassium iodide (0.5 g). The mixture was refluxed overnight. Inorganic salts were filtered off and MIBK was evaporated. The remaining oil was purified by column chromatography on silica gel (eluted with heptan/ethyl acetate 2:3). Yield of the title compound as an oil 1.6 g. $^1$H NMR (CDCl$_3$) δ1.35 (t, 3H), 1.35–1.50 (m, 2H), 1.60–1.75 (m, 3H), 1.90–2.05 (m, 3H), 2.20 (s, 3H), 2.35–2.60 (m, 4H), 3.60 (t, 1H), 3.85 (t, 1H), 4.25 (q, 2H), 6.95 (t, 4H), 7.15

The following 3-ethoxy derivative was prepared in a corresponding manner:

(R,S)-4-[-N-(4,4-Diphenylbut-1-yl)-N-methylamino]-3-ethoxy-4,5,6,7-tetrahydro-1,2-benzisoxazole, 10b. Prepared via alkylation with 4,4-Diphenyl-1-butyliodide, 29a and isolated as an oil. $^1$H NMR (CDCl$_3$) δ1.30 (t, 3H), 1.35–1.50 (m, 2H), 1.60–1.70 (m, 4H), 1.90–2.10 (m, 2H), 2.15 (s, 3H), 2.30–2.50 (m, 4H), 3.55 (t, 1H), 3.85 (t, 1H), 4.25 (q, 2H), 7.10–7.30 (m, 10H).

The following compounds were prepared in a similar manner exept that the alkylations were performed in acetone without addition of potassium iodide.

(R,S)-4-[N-[3-(10,11-dihydrodibenzo[a,d]cyclohept-5-ylidene)propane-1-yl]methylamino]-3-ethoxy-4,5,6,7-tetrahydro-1,2-benzisoxazole, 10c. Prepared via alkylation with 3-(10,11-dihydrodibenzo[a,d]cyclohept-5-ylidene)-1-propylbromide (prepared as described in J. Org. Chem. (1962), Vol. 27, 4134–37) and isolated as an oil. $^1$H NMR (CDCl$_3$) δ1.30 (t,3H), 1.60–1.74 (m,3H), 1.87–2.06 (m,1H), 2.20 (s,3H), 2.20–2.35 (m,2H), 2.45–2.70 (m,4H), 2.70–3.50 (m,4H), 3.50–3.63 (m,1H), 4.24 (q,2H), 5.88 (t,1H), 6.98–7.30 (m,8H)

(R,S)-4-[N-[4,4-Di-(2-tolyl)butan-1-yl]-methylamino]-3-ethoxy-4,5,6,7-tetrahydro-1,2-benzisoxazole, 10d. Prepared via alkylation with 4,4-di-(2-tolyl)-1-butyliodide, 34a and isolated as an oil. $^1$H NMR (CDCl$_3$) δ1.28 (t,3H), 1.42–1.56 (m,2H), 1.60–1.80 (m,4H), 1.87–2.05 (m,3H), 2.20 (s,3H), 2.26 (dd,6H), 2.35–2.60 (m,4H), 3.60 (t,1H), 4.23 (q,2H), 7.00–7.17 (m,8H)

(R,S)-4-[N-[1,1-Di-(2-tolyl)but-1-en-4-yl]methylamino]-3-ethoxy-4,5,6,7-tetrahydro-1,2-benzisoxazole, 10e. Prepared via alkylation with 4,4-di-(2-tolyl)-3-butenyliodide, 36a and isolated as an oil. $^1$H NMR (CDCl$_3$) δ1.33 (t,3H), 1.55–1.80 (m,4H), 1.90–2.07 (m,2H), 2.17 (dd,6H), 2.26 (s,3H), 2.45–2.67 (m,4H), 3.57 (t,1H), 4.26 (q,2H), 5.81 (t,1 H), 7.00–7.17 (m,8H)

EXAMPLE 11 (METHOD C))

(R,S)-4-[N-[4,4-Bis(4-fluorophenyl)butan-1-yl]-N-methylamino]-3-hydroxy-4,5,6,7-tetrahydro-1,2-benzisoxazole, hydrobromide 11a All of the product 10a (1.6 g) from Example 10 was heated at 80° C. in a 33% solution of hydrogen bromide in glacial acetic acid (60 mL) for 1 hour. The solvent was evaporated in vacuo. The remaining crude product was repeatedly dissolved in ethanol and evaporated in vacuo. The remaining visceous oil was dissolved in glacial acetic acid (15 mL) and water (150 mL) was added. After freez-edrying overnight, an amorpheous powder of the title compound 11a remained. This powder was stirred with diethyl ether and filtered off. After drying in vacuo at 50° C. for 24 hours, the pure amorpheous hydrobromide was collected. Yield 1.2. Mp 68–70° C. $^1$H NMR (DMSO-d$_6$ recorded at 60° C.) δ1.60–2.15 (m, 8H), 2.55–2.70 (m, 2H), 2.70 (broad s, 3H), 3.20 (broad t, 2H), 4.05 (t, 1H), 4.45 (t, 1H), 7.10 (t, 4H), 7.35 (dd, 4H), MS m/z (%): 413 (MH+, 10%), 203 (13%), 138 (100%), 109 (12%), 67 (58%).

The following 3-hydroxy derivative was prepared in a corresponding manner:

(R,S)-4-[-N-(4,4-Diphenylbut-1-yl)-N-methylamino]-3-hydroxy-4,5,6,7-tetrahydro-1,2-benzisoxazole, hydrobromide 11b. Mp 174–176° C. (ethanol/diethyl ether 1:1). $^1$H NMR (DMSO-d$_6$) δ1.50–2.10 (m, 6H), 2.60–2.80 (m, 4H), 3.15–3.40 (m, 2H), 3.30 (s,3H), 3.95 (t, 1H), 4.40 (broad s, 1H), 7.15–7.45 (m, 10H). MS m/z (%): 377 (MH+, 100%), 240(56%), 138 (49%).

EXAMPLE 12

(R,S)-4-(N-tert-Butyloxycarbonyl-N-methylamino)-3-hydroxy-4,5,6,7-tetrahydro-1,2-benzisoxazole 12a To a solution of (R,S)-3-hydroxy-4-methylamino-4,5,6,7-tetrahydro-1,2-benzisoxazole, hydrobromide 8a (7.0 g) in a mixture of dioxane (50 mL) and water (80 mL) were added at 10° C. NaOH (1.1 g) and a solution di-tert-butyidicarbonate (6.0 g) in dioxane (20 mL). The mixture was stirred at room temperature for 1.5 hours. Water (150 mL) was added. After stirring for additionally 20 minutes diethyl ether (100 mL) was added. The organic phase was separated and discarded. pH of the aqueous phase was adjusted to 4 by addition of KHSO$_4$. The aqueous phase was repeatedly extracted with diethyl ether (3×100 ml). The combined organic phases were worked up as above. Yield 5.3 g. Mp 151–152° C. $^1$H NMR (CDCl$_3$) δ1.50 (s, 9H), 1.65–2.10 (m, 4H), 2.55–2.65 (m, 2H), 2.75 (s, 3H), 5.15 (broad s, 1H).

By the same method was synthesized:

(R,S)-4-(tert-Butyloxycarbonylamino)-3-hydroxy-4,5,6, 7-tetrahydro-1,2-benzisoxazole 12b. Mp 175–177° C. (from ethyl acetate-light petroleum).

EXAMPLE 13

(R,S)-4-(N-tert-butyloxycarbonyl-N-methylamino)-3-pivaloyloxymethyloxy-4,5,6,7-tetrahydro-1,2-benzisoxazole 13a To a suspension of (R,S)-4-(N-tert-butyloxycarbonyl-N-methylamino)-3-hydroxy-4,5,6,7-tetrahydro-1,2-benzisoxazole 12a (5 g) in acetone (50 mL) was added catiously (temperature below 30° C.) potassium tert-butoxide (2.5 g). A solution of pivaloyloxymethyliodide (7.5 g) in acetone (10 mL) was added and the mixture was stirred overnight. Inorganic salts were filtered off and the acetone evaporated. Column chromatography on silica gel (eluted with heptane/ethyl acatate 3:2) yielded 3.9 g of the title compound 13a as an oil. $^1$H NMR (CDCl$_3$) δ1.30 (s, 9H), 1.50 (s, 9H), 1.50–2.10 (m, 6H), 2.50–2.60 (m, 5H), 5.00–5.30 (broad signal, 1H), 5.85 (dd, 2H).

A more polar fraction from the column chromatography contained 2.1 g of (R,S)-4-(N-tert-butyloxycarbonyl-N-methylamino)-2-pivaloyloxymethyl-4,5,6,7-tetrahydro-1,2-benzisoxazol-3-one 13b. $^1$H NMR (CDCl$_3$) δ1.20 (s, 9H), 1.50 (s, 9H), 1.60–2.10 (m, 4H), 2.40–2.50 (m, 2H), 2.65 (s, 3H), 5.00–5.10 (broad signal, 1H), 5.75 (s, 2H).

The following compounds were synthesized correspondingly:

(R,S)-4-(tert-Butyloxycarbonylamino)-3-pivaloyloxymethyloxy-4,5,6,7-tetrahydro-1,2-benzisoxazole 13c (oil). $^1$H-NMR (CDCl$_3$) δ1.25 (s,9H), 1.45 (s,9H), 1.80–1.95 (m,4H), 2.50–2.75 (m,2H), 4.75 (broad s, 2H), 5.90 (s,2H).

(R,S)-4-(tert-Butyloxycarbonylamino)-2-pivaloyloxymethyl-4,5,6,7-tetrahydro-1,2-benzisoxazole 13d (oil). $^1$H-NMR (CDCl$_3$) δ1.20 (s,9H), 1.45 (s,9H), 1.80–2.00 (m,4H), 2.30–2.55 (m,2H), 4.50–4.90 (m,2H), 5.75 (s,2H).

EXAMPLE 14

(R,S)-4-methylamino-3-pivaloyloxymethyloxy-4,5, 6,7-tetrahydro-1,2-benzisoxazole, hemioxalate 14a (Method a))

To a solution of (R,S)-4-(N-tert-butyloxycarbonyl-N-methylamino)-3-pivaloyloxymethyloxy- 4,5,6,7-tetrahydro-1,2-benzisoxazole 13a (3.7 g) in dichloromethane kept at 20° C. was added trifluoroacetic acid (19 mL). The mixture was stirred at 20° C. for another hour. The solvents were evaporated at room temperature in vacuo. The remaining oil was dissolved in diethyl ether (100 mL) and water (100 mL). Potassium carbonate was added to obtain pH>9. The organic phase was separated and worked up as above. Yield of crude title compound as the free base 2.4 g. To a solution of all of the base of 14a in ethanol (10 mL) was added oxalic acid (0.7 g). The precipitated hemioxalate salt was filtered off. Yield 1.2 g. Mp 201–202° C. $^1$H NMR (DMSO-d$_6$) δ1.15 (s, 9H), 1.65–2.05 (m, 4H), 2.40 (s, 3H), 2.55–2.80 (m, 2H), 3.85 (t, 1H), 5.90 (dd, 2H). MS m/z (%): 283 (MH+), 138 (30%), 57 (100%).

In a corresponding way from (R,S)-4-(N-tert-butyloxycarbonyl-N-methylamino)-2-pivaloyloxymethyl-4,5,6,7-tetrahydro-1,2-benzisoxazol-3-one (13b) was isolated (R,S)-4-methylamino-2-pivaloyloxymethyl-4,5,6,7-tetrahydro-1,2-benzisoxazol-3-one, hemioxalate 14b. Mp 177–178° C. (from acetone). $^1$H NMR (DMSO-$d_6$) δ1.15 (s, 9H), 1.60–2.05 (m, 4H), 2.50 (s, 3H), 2.45–2.60 (m, 2H), 3.80 (t, 1H), 5.80 (dd, 2H). MS m/z (%): 283 (MH+), 123 (52%), 57 (52%), 55 (100%).

Similarly, treatment of (R,S)-4-(tert-Butyloxycarbonylamino)-3-pivaloyloxy-methyloxy-4,5,6,7-tetrahydro-1,2-benzisoxazole 13c with a 2.5M solution of HCl inethyl acetate afforded (R,S)-4-amino-3-pivaloyloxymethyloxy-4,5,6,7-tetrahydro-1,2-benzisoxazole hydrochloride 14c. Mp 157–168° C. (from acetonitrile-ether). 1H-NMR (CDCl$_3$) δ1.20 (s,9H), 2.0–2.35 (m,4H), 2.50–2.85 (m,2H), 4.25–4.50 (m, 1H), 5.90 (s,2H).

The enantiomers of compound 14a were prepared as follows:

From (+)-3-hydroxy-4-methylamino-4,5,6,7-tetrahydro-1,2-benzisoxazole, hydrobromide, 6c, the corresponding enantiomer of 4-(N-tert-butyloxycarbonyl-N-methylamino)-3-hydroxy-4,5,6,7-tetrahydro-1,2-benzisoxazole was prepared by reaction with di-tert-butyidicarbonate according to the procedure in Example 12. Further reaction with pivaloyloxymethyliodide as in Example 13 gave the pure isomer of 4-(N-tert-butyloxycarbonyl-N-methylamino)-3-pivaloyloxymethyloxy-4,5,6,7-tetrahydro-1,2-benzisoxazole. As previously described (Example 14) the BOC-protecting group was splitted off by treatment with trifluoroacetic acid. The pure enantiomer A of compound 14a crystallized from acetone as the hemioxalate salt. Mp 211–213° C. The optical rotation was $[\alpha]_D$=–5.4° (C=1, MeOH).

In a corresponding way from compound 6d the other isomer was prepared: 4-Methylamino-3-pivaloyloxymethyloxy-4,5,6,7-tetrahydro-1,2-benzisoxazole, hemioxalate, enantiomer B, Mp 210–213° C. The optical rotation was $[\alpha]_D$=+5.6° (C=1, MeOH).

To prove the enantiomeric purity both compounds were analysed by $^1$H NMR in the presence of R(–)-1-(9-anthryl)-2,2,2-trifluoroethanol. There is a splitting of the singlets from the tert-butyl group and the methyl group both into two singlet signals for the racemate. Enantiomer A gave singlets at δ (ppm) 1.15 (s, 9H) and 2.15 (s, 3H). Enantiomer B gave singlets at δ (ppm) 1.20 (s, 9H) and 2.25 (s, 3H). No impurities from the other isomer was detected in the two compounds. The detection limit was estimated to be 2%.

EXAMPLE 15
(Method a))

(R,S)-4-methylamino-2-phenylaminocarbonyl-4,5,6,7-tetrahydro-1,2benzisoxazol-3-one, hydrochloride 15a To a solution of (R,S)-4-(N-tert-butyloxycarbonyl-N-methylamino)-3-hydroxy-4,5,6,7-tetrahydro-1,2-benzisoxazole 12a (1.0 g) in dichloromethane (10 mL) was added phenylisocyanate (0.6 mL). The mixture was stirred overnight at room temperature. Dichloromethane was evaporated. (R,S)-4-(N-tert-butyloxycarbonyl-N-methylamino)-2-phenylaminocarbonyl-4,5,6,7-tetrahydro-1,2-benzisoxazol-3-one crystallized from diethyl ether. The said crystallized compound (0.4 g) was suspended in a saturated solution of hydrogen chloride in diethyl ether. After a few minutes of stirring almost all of the compound had dissolved and the hydrochloride salt of the title compound started precipitating. After stirring for 2 hours the precipitated title compound was filtered off and carefully washed with diethyl ether. Yield 0.3 g. Mp 168–170° C. $^1$H NMR (DMSO-$d_6$) δ1.65–2.05 (m, 2H), 2.15–2.30 (m, 2H), 2.65 (s, 3H), 2.60–2.80 (m, 2H), 4.20 (broad s, 1H), 7.20 (t, 1H), 7.40 (t, 2H), 7.55 (d, 2H).

The following compounds were prepared in a corresponding way:

(R,S)-2-Methylaminocarbonyl-4-methylamino4,5,6,7-tetrahydro-1,2-benzisothiazol-3-one, oxalate 15b. Mp: 153° C. (acetone). $^1$H NMR (DMSO-$d_6$) δ1.75–2.15 (m, 4H), 2.60–2.70 (m, 2H), 2.65 (s, 3H), 2.85 (d, 3H), 4.15 (broad s, 1H), 7.80 (q, 1H), 9.15 (broad s, 3H). MS m/z (%): 226 (MH+), 160 (9%), 138 (57%), 67 (100%), 65 (50%). (R,S)-2-Benzylaminocarbonyl-4-methylamino-4,5,6,7-tetrahydro-1,2-benzisothiazol-3-onehydrochlorid 15c. Mp: 85–89° C. (diethyl ether). $^1$H NMR (DMSO-$d_6$) δ1.80–2.05 (m, 2H), 2.10–2.30 (m, 2H), 2.60–2.80 (m, 2H), 2.65 (s, 3H), 4.15 (broad s, 1H), 4.45 (d, 2H), 7.20–7.40 (m, 5H), 8.45 (t,1 H), 9.30–9.60 (broad d, 2H). MS m/z (%): 302 (MH+), 169 (8%), 138(58%), 91 (97%), 65 (100%).

EXAMPLE 16

(R,S)-4-[N-[bis(4-fluorophenyl)methyl-2-oxyethyl]-N-methylamino]-3-hydroxy-4,5,6,7-tetrahydro-1,2-benzisoxazole, sodium salt 16a (method c))

To a solution of (R,S)-4-methylamino-3-pivaloyloxymethyloxy-4,5,6,7-tetrahydro-1,2-benzisoxazole 14a (1.1 g) in MIBK (18 mL) were added potassium carbonate (0.7 g), and the methansulfonate ester of bis(4-fluorophenyl)methyl-2-oxyethanol (1.8 g). The mixture was refluxed overnight. Inorganic salts were filtered off and MIBK evaporated. Column chromatoghraphy afforded pure (R,S)-4-[N-[bis(4-fluorophenyl)methyl-2-oxyethyl]-N-methylamino]-3-pivaloyloxymethyloxy-4,5,6,7-tetrahydro-1,2-benzisoxazole. Yield 1.4 g. $^1$H NMR (CDCl$_3$) δ1.20 (s, 9H), 1.60–1.80 (m, 3H), 1.95–2.05 (m, 1H), 2.25 (s, 3H), 2.55 (broad t, 2H), 2.60–2.80 (m, 2H), 3.50 (t, 2H), 3.65 (dt, 1 H), 5.35 (s, 1 H), 5.90 (dd, 2H), 7.00 (t, 4H), 7.30 (dd, 4H), 7.55 (d, 2H), To the pivaloyloxymethyl protected derivative (0.6 g) in ethanol (7 mL) was added water (1.4 mL) and NaOH powder (0.7 g). The mixture was stirred overnight. Ethanol was evaporated in vacuo and water (25 mL) was added. The precipitated crystalline product was filtered off and washed with water. After drying overnight at 70–80° C. in vacuo 350 mg of pure sodium salt of the title compound remained. Mp: 178–81 $^1$H NMR (DMSO-$d_6$) δ1.30–1.90 (m, 2H), 2.15–2.35 (m, 4H), 2.60–2.85 (m, 2H), 3.25 (t, 1H), 3.40 (t, 2H), MS m/z (%): 415 (MH+,4%), 203 (100%), 183 (63%), 138 (42%), 67 (30%).

The following compounds were prepared in a corresponding way:

(R,S)-4-[N-[bis(4-chlorophenyl)methyl-2-oxyethyl]-N-methylamino]-3-hydroxy-4,5,6,7-tetrahydro-1,2-benzisoxazole, sodium salt 16b. Mp: 201–203° C. (water/ethanol). $^1$H NMR (DMSO-$d_6$) δ1.40–1.60 (m, 2H), 1.60–1.70 (m, 1H), 1.75–1.85 (m, 1H), 2.20–2.35 (m, 2H), 2.20 (s, 3H), 2.65–2.90 (m, 2H), 3.35 (t, 1H), 1.75–1.85 (m, 2H), 5.55 (s, 1H), 7.45 (s, 8H). MS m/z (%): 447 (MH+), 235 (78%), 165 (57%), 138 (100%), 67 (56%).

(R,S)-4-[N-(diphenylmethyl-2-oxyethyl)-N-methylamino]-3-hydroxy-4,5,6,7-tetrahydro-1,2- benzisoxazole, hydrochloride 16c. Mp: 108–113° C. (amorphous) (diethyl ether). $^1$H NMR (DMSO-d$_6$) δ1.70–2.10 (m, 2H), 2.10–2.30 (m, 2H), 2.60–2.75 (m, 2H), 2.80 (broad s, 3H), 3.40–3.60 (m, 2H), 3.80 (broad t, 2H), 4.55 (broad s, 1H), 5.55 (s, 1H), 7.20–7.45 (m, 10H). MS m/z (%): 379 (MH+, 4%), 167 (100%), 152 (74%),138 (36%), 67 (32%).

In a similar manner, treatment of (R,S)-4-[N-(4,4-bis[3-methylthien-2-yl]-3-butenyl)-N-methylamino]-3-pivaloyloxymethyloxy-4,5,6,7-tetrahydro-1,2-benzisoxazole with NaOH in aqueous ethanol followed by acidification with 4M HCl and extraction with methylene chloride gave (R,S)-4-[N-(4,4-bis[3-methylthien-2-yl]-3-butenyl)-N-methylamino]-3-hydroxy-4,5,6,7-tetrahydro-1,2-benzisoxazole hydrochloride 16d. Mp 135–138° C. (from acetonitrile-ether). 1H-NMR (DMSO-d$_6$) δ1.95 (s,3H), 2.0 (s,3H), 1.95–2.20 (m,4H), 2.55–2.90 (m,6H), 3.35 (s,3H), 4.40–4.50 (m,1H), 6.0 (t, 1H), 6.85 (d,1H), 6.95 (d, 1H), 7.35 (d,1H), 7.55 (d,1H).

EXAMPLE 17

(R,S)-3-Ethoxy-4-dimethylamino-4,5,6,7-tetrahydro-1,2-benzisoxazole, hydrobromide 17a A mixture of (R,S)-3-ethoxy-4-amino-4,5,6,7-tetrahydro-1,2-benzisoxazole, hydrobromide 3a (526 mg) and 1 M sodium hydroxide (8 mL) was extracted with methylene chloride (3×10 mL). The combined extracts were dried and evaporated. Formic acid (3 mL), 30% formaldehyde (3 mL) and sodium formiate (3 g) were added to the residue and the mixture was stirred at 60° C. for 3 h and at 100° C. for 20 h. After evaporation, water (20 mL) was added to the residue and pH was adjusted to 10 with 2 M sodium hydroxide. The mixture was extracted with methylene chloride (3×40 mL) and the combined extracts were dried and evaporated. The residue was dissolved in ether (25 mL) and an excess of 33% hydrobromic acid in glacial acetic acid was added dropwise to precipitate the title compound (422 mg). Recrystallization from acetonitrile-ether gave an analytical pure compound: mp 158–160° C. $^1$H NMR (60 MHz, D$_2$O) δ1.60 (t, 3H), 2.20 (m, 4H), 2.85 (m, 2H), 3.05 (s, 6H), 4.50 (q, 2H), 4.55 (m, 1 H).

EXAMPLE 18

(R,S)-4-Dimethylamino-3-hydroxy-4,5,6,7-tetrahydro-1,2-benzisoxazole, hydrobromide 18a (Method c))

A solution of (R,S)-3-ethoxy-4-dimethylamino-4,5,6,7-tetrahydro-1,2-benzisoxazole hydrobromide 17a (250 mg) and 33% hydrobromic acid in glacial acetic acid (5 mL) was stirred at 80° C. for 25 min. The mixture was evaporated and 33% hydrobromic acid in glacial acetic acid (5 mL) was added to the residue. After being stirred at 80° C. for 25 min, the mixture was evaporated and the residue recrystallized from acetonitrile-ethanol-ether to give the title compound (199 mg): mp 183–186° C. The compound crystallized with 0.33 mol of water. $^1$H NMR (60 MHz, D$_2$O) δ2.35 (m, 4H), 3.00 (m, 2H), 3.25 (s, 6H), 4.70 (m,1H).

EXAMPLE 19

(R,S)-3-Benzyloxy-4-methylamino-4,5,6,7-tetrahydro-1,2-benzisoxazole, hydrochloride 19a A mixture of (R,S)-3-hydroxy-4-(N-methyl-N-tert-butyloxycarbonylamino)-4,5,6,7-tetrahydro-1,2-benzisoxazole 12a (1.20 g) and potassium carbonate (1.23 g) in DMF (25 mL) was stirred at 40° C. for 45 min. Benzyl bromide (1.59 mL) was added and stirring at 40° C. was continued for 20 h. The reaction mixture was evaporated and water (25 mL) was added to the residue. Extraction with methylene chloride (3×50 mL), drying and evaporation gave an oil. Flash chromatography on silica gel (eluent:toluene containing ethyl acetate (0–75%)) eluted (R,S)-3-benzyloxy-4-(N-methyl-N-tert-butyloxycarbonylamino)-4,5,6,7-tetrahydro-1,2-benzisoxazole (oil, 620 mg). A mixture of the said compound (620 mg), 1M HCl (15 mL) and ethanol (20 mL) was stirred at 45° C. for 80 min. Evaporation and recrystallization of the residue from acetonitrile-ether gave the title compound (460 mg). Mp 156–159° C.

The following compound was synthesized correspondingly:

(R,S)-3-Benzyloxy-4-amino-4,5,6,7-tetrahydro-1,2-benzioxazole hydrochloride 19b.

Mp 168–170° C.

EXAMPLE 20

(R,S)-3-Hydroxy-4-[N-(4,4-diphenyl-3-butenyl) methylamino]-4,5,6,7-tetrahydro-1,2-benzisoxazole, hydrochloride 20a (Method c))

A mixture of Compound 19a (442 mg), potassium carbonate (622 mg), sodium iodide (50 mg) and 4,4-diphenyl-3-butenyl bromide (646 mg) in DMF (8 mL) was stirred at 120° C. for 24 h. A solution of 4,4-diphenyl-3-butenyl bromide (500 mg) in DMF (3 mL) was added and stirring at 120° C. was continued for 24 h. The reaction mixture was evaporated and water (20 mL) was added to the residue. Extractions with ether (3×25 mL), drying and evaporation gave an oil. Flash chromatography on silica gel (eluent: toluene-ethyl acetate (0–100%)) gave (R,S)-3-benzyloxy-4-[N-(4,4-diphenyl-3-butenyl)methylamino]-4,5,6,7-tetrahydro-1,2-benzisoxazole (590 mg) as a light-yellow oil. A solution of the said compound (590 mg) in ethanol (16 mL) and concentrated hydrochloric acid (8 mL) was refluxed for 3 days. Evaporation and recrystallization of the residue from acetone-ethanol-ether gave the title compound (212 mg). Mp. 119–120° C. $^1$H NMR (D$_2$O and DMSO-d$_6$) δ1.60–1.98 (m, 4H), 2.35–2.6 (m, 2H), 2.58 (s, 3H), 3.10 (m, 2H), 4.18 (m, 1H), 5.91 (t, 7.0–7.4 (m, 10H). The $^1$H NMR spectrum showed the presence of 0.75 equivalent of ethanol.

The following compounds were synthesized correspondingly:

(R,S)-3-Hydroxy-4-[N-(4,4-diphenyl-3-butenyl)amino]-4,5,6,7-tetrahydro-1 2-benzioxazole hydrochloride hydrate 20b. Mp 140–143° C. (from acetonitrile). $^1$H-NMR (D$_2$O and DMSO-d$_6$) δ1.80–2.20 (m,4H), 2.40–2.60 (m,4H), 3.10–3.30 (m,2H), 4.15–4.30 (m,1H), 6.10 (t,1H), 7.10–7.45 (m,10H).

(R,S)-3-Hydroxy-4-[N-(4,4-bis[3-methylthien-2-yl]-3-butenyl)amino]-4,5,6,7-tetrahydro-1,2-benzisoxazole hydrochloride 20c. Mp 188–191° C. (from ethanol-acetonitrile). 1H-NMR (D$_2$O and DMSO-d$_6$) δ1.85–2.15 (m,4H), 2.05 (s,3H), 2.08 (s,3H), 2.45–2.90 (m,4H), 3.15–3.30 (m,2H), 4.20–4.35 (m,1H), 6.10 (t,1H), 6.90 (m, 1 H), 7.0 (m, 1H), 7.25 (t, 1H), 7.40 (t, 1H).

EXAMPLE 21

2-Benzylamino-3,4,5,6-tetrahydrobenzamide 21a

A mixture of cyclohexanone-2-carboxamide (U.S. Pat. No. 4,169,952 to du Pont de Nemours, (1979)) (10.0 g), benzylamine (8.4 g), toluene (35 mL) and molecular sieves (Union Carbide 3A, 2 g) was refluxed for 2 h in a Dean-Stark water separator. The reaction mixture was filtered, and the filtrate was evaporated. The residue was crystallized from light petroleum to give the title compound (16 g). Mp 73–74° C.

EXAMPLE 22

3-Hydroxy-4,5,6,7-tetrahydro-1,2-benzisothiazole 22a

To a solution of 2-benzylamino-3,4,5,6-tetrahydrobenzamide 21a (15 g) in glacial acetic acid (100 mL) was added excess hydrogen sulfide at 80° C. for 4 h. The reaction mixture was evaporated and ether was added to the residue which afforded crystallisation. The crystals were dissolved in ethyl acetate (30 mL) and a solution of bromine (8.3 mL) in ethyl acetate (30 mL) was dropwise added at room temperature. The mixture was stirred for 20 h at room temperature and evaporated. Column chromatography on silica gel (eluent:ethyl acetate-ethanol 1:1 containing 1% glacial acetic acid) gave the title compound (3.3 g): mp 157–158° C.

EXAMPLE 23

3-Chloro-4,5,6,7-tetrahydro-1,2-benzisothiazole 23a

A mixture of 3-hydroxy-4,5,6,7-tetrahydro-1,2-benzisothiazole 22a (4.74 g), pyridinium hydrochloride (12.7 g), phosphoric acid (2.1 g) and phosphorus oxychloride (25 mL) was stirred at 90° C. for 5 h. The reaction mixture was evaporated and ethyl acetate (130 mL) was added to the residue. A saturated solution of sodium hydrogencarbonate (130 mL) was added and after 10 min of stirring the phases were separated. The aqueous phase was extracted with ethyl acetate (2×150 mL) and the combined organic phases were dried and evaporated to give an oil. Column chromatography on silica gel (eluent:toluene-ethyl acetate 1:1) gave the title compound as a yellow oil (2.8 g).

EXAMPLE 24

3-Chloro-4,5,6,7-tetrahydro-1,2-benzisothiazol-4-one 24a

A solution of sodium dichromate (4.4 g) in glacial acetic acid (30 mL) was added dropwise over 1 h to a solution of 3-chloro-4,5,6,7-tetrahydro-1,2-benzisothiazole 23a (2.7 g) and concentrated sulfuric acid (1.8 mL) in glacial acetic acid (80 mL). The reaction mixture was stirred at room temperature for an additional 2 h, and neutralized with a saturated solution of sodium hydrogencarbonate. Extraction with ether (3×150 mL), drying and evaporation gave an oil. Column chromatography on silica gel (eluent: toluene-ethyl acetate 1:1) eluted first 3-chloro-4,5,6,7-tetrahydro-1,2-benzisothiazol-7-one (680 mg). The later fractions contained the title compound (780 mg). Mp 84–85° C.

EXAMPLE 25

3-Methoxy-4, 5,6,7-tetrahydro-1,2-benzisothiazol-4-one 25a

A mixture of 3-chloro-4,5,6,7-tetrahydro-1,2-benzisothiazol-4-one 24a (600 mg) and a solution of sodium (506 mg) in methanol (22 mL) was stirred at 90° C. for 1 h. The reaction mixture was evaporated and water (20 mL) was added to the residue. Extractions with methylene chloride (3×30 mL), drying and evaporation gave an oil. Column chromatography on silica gel (eluent:toluene-ethyl acetate 4:1) gave the title compound (251 mg). Mp 45–46° C.

EXAMPLE 26

(Method c)

(R,S)-4-Amino-3-hydroxy-4,5,6,7-tetrahydro-1,2-benzisothiazole, hydrobromide 26a To a solution of 3-methoxy-4,5,6,7-tetrahydro-1,2-benzisothiazol-4-one 25a (185 mg) and ammonium acetate (780 mg) in methanol (7 mL) was portionwise added sodium borohydride (44 mg). The mixture was stirred at room temperature for 48 h and acidified with concentrated hydrochloric acid. The mixture was evaporated and water (3 mL) was added to the residue. The aqueous solution was washed with ether (3×15 mL) and solid potassium hydroxide was added until pH >10. Extraction with ether (3×15 ml), drying and evaporation gave an oil. The oil was dissolved in ethanol and excess of hydrochloric acid in ethyl acetate was added to precipitate (R,S)-3-methoxy-4-amino-4,5,6,7-tetrahydro-1,2-benzisothiazole, hydrochloride (68 mg). A solution of 33% hydrobromic acid in glacial acetic acid (3 mL) was added to the said hydrochloride (60 mg) and the mixture was stirred at room temperature for 48 h. Evaporation and recrystallizations of the residue (methanol-ether) gave the title compound (28 mg). Mp 160–165° C. $^1$H NMR (D$_2$O) δ1.78–2.04 (m, 3H), 2.05–2.28 (m, 1H), 2.72–2.87 (m, 2H), 4.23–4.39 (m, 1 H).

EXAMPLE 27

(R,S)-3-Hydroxy-4-methylamino-4,5,6,7-tetrahydro-1,2-benzisothiazole, hydrobromide 27a (R,S)-3-Methoxy-4-methylamino-4,5,6,7-tetrahydro-1,2-benzisothiazole was synthesized as described for Compound 7a in Example 7 using Compound 25a (200 mg) in methanol (5 mL), a 33% solution of methylamine (217 μL) in ethanol, molecular sieves (3 Å) powder and sodium cyanoborohydride (234 mg). The resulting oil was dissolved in ether and excess of hydrochloric acid in ethyl acetate was added to precipitate (R,S)-3-methoxy-4-methylamino-4,5,6,7-tetrahydro-1,2-benzisothiazole hydrochloride (172 mg), mp 146–148. A solution of hydrobromic acid in glacial acetic acid (33%, 6 mL) was added to 100 mg thereof and the mixture was stirred at room temperature for 48 hours. Evaporation and recrystaflization of the residue from methanol-ether gave the title compound (53 mg), mp 192° C. (dec.). $^1$H-NMR (200 MHz, D$_2$O): δ1.82–2.24 (m, 4H), 2.72 (s, 3H), 2.68–2.92 (m, 2H), 4.16–4.30 (1H).

EXAMPLE 28

(Method e)

(R,S)-3-Hydroxy-N-methyl-N-(4-phenyloxycarbonyl)amino-4,5,6,7-tetrahydro-1,2-benzisoxazole 28a To a solution of (R,S)-3-hydroxy-N-methylamino-4,5,6,7-tetrahydro-1,2-benzisoxazole, hydrobromide (1.0 g) and triethylamine (1.8 mL) in dry dimethylformamide (10 mL) kept at 0° C. was added dropwise phenyl chloroformate (0.7 g) in THF (10 mL). After stirring overnight at room temperature water (200 mL) and ethyl acetate (100 mL) were added. PH was adjusted to 1–2 by addition of hydrochloric acid. The organic phase was separated and worked up as above. The title compound crystallized by stirring with diethyl ether. Yield 1.0 g. Mp 147–149° C. $^1$H NMR (CDCl$_3$) δ1.70–1.95 (m, 2H), 2.05–2.20 (m, 2H), 2.6–2.7 (m, 2H), 2.85 (s, 1H), 2.95 (s, 2H), 5.35 (broad s, 1H), 7.10–7.40 (m, 5H), 8.05 (broad s, 1H). MS m/z (%): 289 (MH+, 10%), 138 (100%), 95 (24%), 67 (77%).

EXAMPLE 29

4,4-Diphenyl-1-butyliodide, 29a

To a suspension of magnesium turnings (15 g) in dry THF (75 mL) was added a little bromobenzene (0.5 g). After an initial exothermic reaction had started, the mixture was heated to reflux and a solution of bromobenzene (90 g) in dry THF (200 mL) was added dropwise during 30 minutes. The mixture was heated for additionally 1.5 hours. The mixture was cooled to room temperature and excess Mg was filtered off in an inert atmosphere. A solution of 4-chlorobutyric acid methylester (40 g) in dry THF (160 mL) was added dropwise at 15–25° C. After further stirring for 30 minutes, the mixture was poured into an aqueous solution of NH$_4$Cl and ice. Diethyl ether (500 mL) was added. The organic phase was worked-up according to the standard workup procedure. Yield 65 g of crude 4-chloro-1,1-diphenylbutan-1-ol. The crude alcohol (30 g) was dissolved in a mixture of glacial acetic acid (60 mL) and 57% aqueous iodic acid (60 mL). Red phosphorus (5 g) was added and the mixture was refluxed for 6 hours. After slowly cooling to room temperature, the mixture was poured into water and diethyl ether. The organic phase was worked up following the standard procedure above yielding 39 g of the title butyliodide 29a as an oil, which was used without further purification.

EXAMPLE 30

4,4-Diphenyl-1-butylamine, hydrochloride 30a

To a solution of 4,4-Diphenyl-1-butyliodide, 29a (20 g) in dry DMF (150 mL) was added sodium azide (10 g). After reflux for 1.5 hours, the mixture was cooled to room temperature and subsequently poured into diethyl ether and water. The organic phase was worked up following the standard procedure above. Yield of 4,4-diphenyl-1-butylazide 14 g. The crude azide (10 g) was dissolved in ethanol (150 mL), water (10 mL) and glacial acetic acid (10 mL). 2% Palladium on Carbon black was added and the mixture was hydrogenated in a Parr apparatus at 3 ato for 1.5 hours. The catalyst was filtered off and the solvents evaporated in vacuo. The remaining viscous oil was dissolved in water and dichloromethane. Aqueous NaOH solution was added to adjust the pH to >11. The organic phase was separated and worked according to the standard procedure above. The hydrochloric salt was prepared by addition of HCl to a solution of the free amino compound in diethyl ether. Yield 3.4 g. Mp 172–175° C.

The following compounds were prepared in a similar manner exept that the amines were not precipitated as hydrochloric salts.

4,4-Di-(2-tolyl)-1-butylamine, 30b. Prepared via the 4,4-di-(2-tolyl)-1-butyliodide, 33a and isolated as an oil. $^1$H NMR (CDCl$_3$) δ1.20 (s broad, 2H), 1.42–1.58 (m,2H), 1.87–2.03 (m,2H), 2.27 (s,6H), 2.70 (t,2H), 4.23 (t,1H), 7.05–7.16 (m,8H) 4,4-Di-(2-tolyl)-3-butenylamine, 30c. Prepared via the 4,4-di-(2-tolyl)-3-butenyliodide 36a and isolated as an oil. $^1$H NMR (CDCl$_3$) δ1.20 (s broad, 2H), 2.11 (s,3H), 2.18 (q,2H), 2.26 (s,3H), 2.77 (t,2H), 5.75 (t,1H), 7.02–7.18 (m,8H).

EXAMPLE 31

(R,S-3-Benzoyloxymethyloxy-4-methylamino-4,5,6, 7-tetrahydro-1,2-benzisoxazole, hemioxalate 31a A mixture of benzoylchloride (22 g), paraformaldehyde (6 g), and a few crystals of ZnCl$_2$ were heated at 100–105° C. for 2.5 hours. Crude benzoyloxymethylchloride was isolated by elution of the reaction mixture through silica gel (eluted with heptane/dichloromethane 1:1). Yield 12 g. All of the crude chloride was dissolved in acetone (100 mL) and sodiumioclide was added. After reflux for 7 hours acetone was evaporated in vacuo and crude benzoyloxymethyliodide was isolated by extraction with diethyl ether from water containing sodium thiosulfate by standard work up procedure. The pure iodide derivative was isolated by column chromatography on silica gel (eluted with heptane/dichloromethane 1:1). Yield 5 g. To a solution of (R,S)-4-(N-tert-Butyloxycarbonyl-N-methylamino)-3-hydroxy-4,5, 6,7-tetrahydro-1,2-benzisoxazole 12a (1.5 g) in acetone (30 mL) in an inert nitrogen atmosphere was added potassium tert-butoxide (0.8 g). The mixture was cooled to 10° C. and a solution of benzoyloxymethyliodide (2.5 g) was added. The mixture was stirred overnight at room temperature in the dark. Acetone was evaporated in vacuo and the remaining crude product was purified by column chromatography on silica gel (eluted with heptane/ethyl acetate 7:3). Yield 1.3 g as an oil. The tert-BOC protecting group was removed as described above by treatment with trifluoroacetic acid in dichloromethane. After evaporation of the solvents the crude product was dissolved in ice cooled water, pH was adjusted to 9–10 by addition of diluted aqueous potassium carbonate. Extraction with diethyl ether and work up of the organic phase using the standard procedure above afforded 1 g of crude title product. The hemioxalate salt 31a crystallized from acetone. Yield 900 mg. Mp 188–189° C. $^1$H NMR (DMSO-d$_6$) δ1.60–2.05 (m, 4H), 2.45 (s, 3H), 2.55–2.80 (m, 2H), 3.85 (t, 1H), 6.15 (s, 1H), 7.60 (t, 2H), 7.65–7.75 (m, 1H), 8.00 (dd, 2H). MS m/z (%): 303 (MH+), 198 (17%), 105 (100%).

In a corresponding manner were prepared the following 3-subtituted derivatives:

(R,S)-4-Methylamino-3-(2,4,6-trimethylbenzoyloxymethyloxy)-4,5,6,7-tetrahydro-1,2-benzisoxazole, hemioxalate 31b. Mp 217° C. (acetone). $^1$H NMR (DMSO-d$_6$) δ1.60–2.05 (m, 4H), 2.20 (s, 6H), 2.25 (s, 3H), 2.45 (s, 3H), 2.55–2.80 (m, 2H), 3.90 (t, 1H), 6.10 (s, 1H), 6.95 (s, 2H). MS m/z (%): 345 (MH+), 240 (100%), 147 (94%).

(R,S)-4-Methylamino-3-(2,6-difluorobenzoyloxymethyloxy)-4,5,6,7-tetrahydro-1,2-benzisoxazole, hemioxalate 31c. Mp 196–197° C. (acetone) $^1$H NMR (DMSO-d$_6$) δ1.60–2.05 (m, 4H), 2,45 (s, 3H), 2.55–2.80 (m, 2H), 3.85 (t, 1H), 6.15 (s, 2H)7.30 (t, 2H), 7.70–7.85 (m, 1H). MS m/z (%): 339 (MH+), 234 (17%), 141 (100%).

(R,S)-4-Methylamino-3-(2-methylbenzoyloxymethyloxy)-4,5,6,7-tetrahydro-1,2-benzisoxazole, hemioxalate 31d. Mp 195–196° C. $^1$H NMR (DMSO-d$_6$) δ1.60–2.05 (m, 4H), 2.40 (s, 3H), 2.50 (s, 3H), 2.55–2.80 (m, 2H), 3.85 (t, 1H), 6.10 (s, 1H), 7.35–7.45 (m, 2H), 7.55 (t, 1H), 7.90 (d, 1H). MS m/z (%): 317 (MH+, 2%), 212 (19%), 119 (100%), 91 (74%).

EXAMPLE 32

(R,S)-4-[N-3-(Phenothiazin-10-yl)propane-1-yl] amino]-3-ethoxy-4,5,6,7-tetrahydro-1,2-benzisoxazole, 32a A solution of 3-ethoxy-4,5,6,7-tetrahydro-1,2-benzisoxazol-4-one 2a (654 mg) and 3-(phenothiazin-10- yl)-1-propylamine (prepared as described in EP-A-0-200-450) (1.02 g) in toluene (130 mL) was boiled under reflux (105° C.) for 6 hrs. p-Toluensulfonic acid, monohydrate (10 mg) was added to the boiling solution which was boiled for additionally 16 hrs. This solution was cooled to 5° C. and was then added to a solution of NaCNBH$_4$ (635 mg) in methanol (50 mL) at 10° C. The resulting reaction mixture was stirred for 20 min, before addition of further NaCNBH$_4$ (500 mg). The reaction mixture was stirred for additional 10 min at 10° C. The reaction mixture was poured onto water and the phases were separated. The aqueous phase was extracted with ethyl acetate (3×250 mL). The combined organic phases were washed with a saturated aqueous NaCl solution, dried (Na$_2$SO$_4$) and evaporated in vacuo. The residue was subjected to CC (n-heptane/ethyl acetate—1:1) to give the title compound as an oil (640 mg). $^1$H NMR (CDCl$_3$) δ1.33 (t,3H), 1.50–2.00 (m,7H), 2.40–2.60 (m,2H), 2.70–2.84 (m,2H), 3.65 (t,1H), 3.97 (t,2H), 4.26 (q,2H), 6.85–6.95 (m,4H), 7.08–7.18 (m,4H)

EXAMPLE 33

2,2-Di-(2-tolyl)-tetrahydrofuran, 33a

To a suspension of magnesium turnings (33 g) in dry THF (150 mL) was added 2-bromotoluene (4 ml ). The reaction mixture was heated to reflux and an exotermic reaction started. The heating mantle was removed and 2-bromotoluene (137 mL) in dry THF (500 mL) was added dropwise over an hour at reflux temperature (exotermic reaction). The resulting reaction mixture was boiled under reflux for additionally 1.5 hrs. The mixture was cooled to room temperature and excess Mg was filtered off in an inert atmosphere. A solution of 4-chlorobutyric acid methylester (56.4 g) in dry THF (200 mL) was added dropwise at 20° C. The reaction mixture was stirred at room temperature for additionally 1 hr and was then poured into an aqueous solution of NH$_4$Cl and ice. The organic phase was worked-up according to the standard workup procedures. After evaporation of the organic solvent the residue was suspended in a mixture of n-heptane/ethyl acetate=4/1. Filtration of the resulting crystals afforded 2,2-di-(2-tolyl)-tetrahydrofuran 33a (32.5 g). $^1$H NMR (CDCl$_3$) δ1.96 (s,6H), 1.96–2.10 (m,2H), 2.57 (t,2H), 4.02 (t,2H), 7.00–7.07 (m,2H), 7.07–7.23 (m,4H), 7.57–7.65 (m,2H)

EXAMPLE 34

4,4-Di-(2-tolyl)-1-butyliodide, 34a

The crude 2,2-di-(2-tolyl)-tetrahydrofuran 33a (28 g) was dissolved in acetic acid (250 mL). 5% palladium on Carbon black (3 g) was added and the mixture was hydrogenated in a Parr apparatus at 3 ato at 55° C. for 5 hrs. The catalyst was filtered off and the solvent was evaporated in vacuo. The remaining oil was subjected to CC (n-heptane/ethyl acetate—15:1) to give 4,4-di-(2-tolyl)-1-butanol (17 g). A solution of 4,4-di-(2-tolyl)-1-butanol (19 g) in acetic acid (400 mL) was boiled under reflux for 3 hrs. The cooled solution was evaporated in vacuo to give 4,4-di-(2-tolyl)-1-butyl acetate (17 g) as an oil. A solution of 4,4-di-(2-tolyl)-1-butyl acetate (9.2 g) in 57% aqueous iodic acid (150 mL) was boiled under reflux for 3 hrs. The cooled solution was poured into a mixture of ice and water and the aqueous phase was extracted with diethyl ether. The combined organic phases were washed with water and a saturated aqueous solution of NaCl, dried (Na$_2$SO$_4$) and evaporated in vacuo to give the title compound 34a (11.7 g) as an oil, which was used without further purification. $^1$H NMR (CDCl$_3$) δ1.80–2.10 (m,4H), 2.28 (s,6H), 3.17 (t,2H), 4.26 (t,1H), 7.12 (s,8H)

EXAMPLE 35

(R,S)-4-[N-[4,4-Di-(2-tolyl)butan-1-yl]amino]-3-ethoxy-4,5,6,7-tetrahydro-1,2- benzisoxazol, 35a The title compound was prepared according to the procedure described in Synlett (1995) 1079–1080 using 4,4-di-(2-tolyl)-1-butylamine 30b (1.7 g), 3-ethoxy-4,5,6,7-tetrahydro-1,2-benzisoxazol-4-one 2a (1.0 g), titanium(IV) isopropylate (4.3 mL), NaCNBH$_3$ (0.6 g) and ethanol (20 mL). The yield of the title compound was 1.0 g which was isolated as an oil. $^1$H NMR (CDCl$_3$) δ1.32 (t,3H), 1.40–1.85 (m,7H), 1.85–2.05 (m,3H), 2.27 (s,6H), 2.45–2.75 (m,4H), 3.68 (t,1H), 4.27 (q,2H), 7.05–7.15 (m,8H)

(R,S)-4-[N-1,1-di-(2-tolyl)but-1-en-4-yl]amino]-3-ethoxy-4,5,6,7-tetrahydro-1,2-benzisoxazol, 35b The title compound was prepared according to the procedure described in Synlett (1995) 1079–1080 using 4,4-di-(2-tolyl)-3-butenylamine, 30c (3.3 g), 3-ethoxy-4,5,6,7-tetrahydro-1,2-benzisoxazol-4-one 2a (2.0 g), titanium(IV) isopropylate (8.2 mL), NaCNBH$_3$ (1.4 g) and ethanol (40 mL). The yield of the title compound was 1.9 g which was isolated as an oil. $^1$H NMR (CDCl$_3$) δ1.33 (t,3H), 1.40–2.05 (m,5H), 2.10 (s,3H), 2.17–2.30 (m,5H), 2.40–2.70 (m,2H), 2.76 (t,2H), 3.67 (t,1H), 4.27 (q,2H), 5.80 (t,1H), 7.03–7.17 (m,8H)

EXAMPLE 36

4,4-Di-(2-tolyl)-3-butenyliodide, 36a

A solution of 2,2-di-(2-tolyl)-tetrahydrofuran 33a (40 g) in 57% aqueous iodic acid (250 mL) was boiled under reflux for 30 min. The cooled solution was extracted wiyh diethyl ether. The combined organic phases were washed with water and a saturated aqueous solution of NaCl, dried (Na$_2$SO$_4$) and evaporated in vacuo. The residue was subjected to CC (n-heptane/ethyl acetate 15:1) to give the title compound 36a as an oil (44 g). $^1$H NMR (CDCl$_3$) δ2.10 (s,3H), 2.30 (s,3H), 2.65 (q,2H), 3.19 (t,2H), 5.73 (t,1H), 7.05–7.22 (m,8H)

EXAMPLE 37

(R,S)-3-Benzenesulfonyloxy-4-(N-tert-butyloxycarbonyl-N-methylamino)-4,5,6,7-tetrahydro-1,2-benzisoxazole, 37a A solution of (R,S)-4-(N-tert-butyloxycarbonyl-N-methylamino)-3-hydroxy-4,5,6,7-tetrahydro-1,2-benzisoxazole 12a (9 g), triethylamine (7.5 mL) and dry THF (350 mL) was cooled to 0° C. Benzenesulfonylchloride (5.2 mL) in dry THF (100 mL) was added dropwise at 0° C. The resulting reaction mixture was stirred for 3 hrs at 0° C. and for 60 hrs at 22° C. The formed precipitate was removed by filtration and the organic solvent was evaporated in vacuo. The residue was subjected to CC (n-heptane/ethyl acetate 1:1) to give the title compound 37a (5.5 g) as an oil. $^1$H NMR (CDCl$_3$) δ1.40–1.94 (m,11H), 1.94–2.14 (m,2H), 2.60–2.72 (m,5H), 4.95–5.36 (m,1H), 7.58 (t,2H), 7.70 (t,1H), 8.02 (d,2H)

EXAMPLE 38

(R,S)-3-Benzenesulfonyloxy-4-methylamino-4,5,6,7-tetrahydro-1,2-benzisoxazole, hydrochloride, 38a To a solution of (R,S)-3-benzenesulfonyloxy-4-(N-tert-butyloxycarbonyl-N-methylamino)-4,5,6,7-tetrahydro-1,2- benzisoxazole, 37a (5.4 g) in dry diethyl ether (100 mL) was added a saturated solution of HCl (g) in dry diethyl ether (50 mL) and the resulting mixture was stirred for 48 hrs at room temperature. The reaction mixture was evaporated in vacuo and the residue was suspended in dry diethyl ether (100 mL). The resulting crystals were collected by filtration and dried to give the title compound 38a (4.0 g). Mp 162–163° C. (dec.). $^1$H NMR (CDCl$_3$) δ1.75–2.15 (m,2H), 2.46–3.04 (m,7H), 4.25 (dd,1H), 7.60 (t,2H), 7.76 (t,1H), 8.03 (d,2H)

EXAMPLE 39

(R,S)-3-Benzenesulfonyloxy-4-[N-methyl-N-(2-propynyl)amino]-4,5,6,7-tetrahydro-1,2-benzisoxazole, 39a A suspension of (R,S)-3-benzenesulfonyloxy-4-methylamino-4,5,6,7-tetrahydro-1,2-benzisoxazole, hydrochloride, 38a (3.5 g) and K$_2$CO$_3$ (4.2 g) in methylisobutylketone (200 mL) was heated to 50° C. for 1 hr. 3-Brom-1-propyne (1.8 mL) in methylisobutylketone (50 mL) was added dropwise at 50° C. The resulting reaction mixture was stirred for additionally 2 hrs at 50° C. and then for 72 hrs at 117° C. (reflux temperature). The cooled mixture was filtered and the solvent was evaporated in vacuo. The residue was subjected to CC (n-heptane/ethyl acetate/triethylamine 14:5:1) to give the title compound 39a (0.92 g). Mp 85–87° C.

$^1$H NMR (CDCl$_3$) δ1.54–2.15 (m,4H), 2.25 (t,1H), 2.33 (s,3H), 2.52–2.77 (m,2H), 3.40 (t,2H), 3.79 (t,1H), 7.57 (t,2H), 7.71 (t,1 H), 8.05 (dd,2H)

EXAMPLE 40

(R,S)-4-(N-tert-butyloxycarbonyl-N-methylamino)-3-ethoxymethyloxy-4,5,6,7-tetrahydro-1,2-benzisoxazole, 40a K$_2$CO$_3$ (2.2 g) was added to at solution of (R,S)-4-(N-tert-butyloxycarbonyl-N-methylamino)-3-hydroxy-4,5,6,7-tetrahyciro-1,2-benzisoxazole 12a (3.5 g) in acetone (200 mL). The resulting suspension was heated to reflux temperature. Ethoxymethylchloride (1.5 g) in acetone (100 mL) was added dropwise at 65° C. and the resulting reaction mixture was boiled under reflux for 2 hrs. The cooled suspension was filtrated and the organic solvent was evaporated in vacuo. The residue was subjected to CC (n-heptane/ethyl acetate/methanol 10:10.1) to give the title compound 40a (0.5 g) as an oil. $^1$H NMR (CDCl$_3$) δ1.24 (t,3H), 1.48 (s,9H), 1.50–2.10 (m,4H), 2.50–2.70 (m,5H), 3.75 (q,2H), 4.90–5.13 (s broad, 1H), 5.20–5.44 (m,2H).

EXAMPLE 41

(R,S)-3-Hydroxy-4-benzylamino-4,5,6,7-tetrahydro-1,2-benzisoxazole hydrobromide 41a Benzaldehyde (0.31 mL) was added to a solution of (R,S)-4-amino-3-ethoxy-4,5,6,7-tetrahydro-1,2-benzisoxazole 3a (from 0.53 g and teh hydrobromide) in ethanol (10 mL). The mixture was stirred at room temperature for 20 min and then cooled in an ice-bath. Sodium boronhydride (0.15 g) was added and the mixture was stirred at 0° C. for 30 min and at room temperature for 20 h. After evaporation, water (10 mL) was added and the mixture was acidified with 4 M HCl. The aqueous solution was washed with ether (2×10 mL) and made basic by addition of 4 M NaOH. Extraction with methylene chloride (3×15 mL), drying and evaporation afforded (R,S)-3-ethoxy-benzylamino-4,5,6,7-tetrahydro-1,2-benzisoxazole (0.31 g). The hydrochloride was prepared by adding a solution of HCl in ethyl acetate and precipitating the hydrochloride by addition of ether. Mp 192–194° C.

Treatment of said compound with HBr as described in Example 8a gave 41a. Mp 202–205° C. 1H-NMR (D$_2$O) δ1.95–2.25 (m,4H), 2.60–2.90 (m,2H), 4.45 (s,2H), 4.35–4.60 (m,1H), 7.55 (s,5H).

The following compound was synthesized correspondingly:

(R,S)-3-Hydroxy-4-(2,2-diphenylethylamino)-4,5,6,7-tetrahydro-1,2-benzisoxazole hydrobromide 41b. Mp 180–183° C. $^1$H-NMR (D$_2$O and DMSO-d$_6$. 1:1) δ1.80–2.15 (m,4H), 2.45–2.75 (m,2H), 3.70–4.00 (m,2H), 4.30–4.65 (m,2H), 7.50 (s,10H), Pharmacology The compounds of the invention were tested in the following well known and recognised test models:

GABA Uptake Synaptosomes

The inhibition of GABA Uptake was performed by the method described by Falch et. al, *Drug Dev. Res.*, 1990,21, 169–188. By this method the overall, i.e. neuronal and glial, inhibition of GABA uptake is determined. The results are shown in the following Table I.

Isoniazid Antagonism

The test is a test for antagonism of isoniazide induced convulsions in mice.

The test substance is given s.c. to mice (male NMRI/BOM, body weight 20–25 g) and 30 min later 300 mg isoniazide is given s.c. Five mice are used per dose and a control group only receiving isoniazide is included. This dose of isoniazide induces intermittent tonic seizures.

The animals are placed individually in Macrolon type II cages and the time when convulsions first occur is recorded. The experiment is stopped after 90 min. The animals that have not had convulsions within 60 min. are recorded as +(protected). The results, i.e. the number of protected mice pr number of tested mice are stated in fractions as follows: 0/5, 1/5, . . . 5/5. The ED$_{50}$ values, calculated by log probit analysis, are shown in Table I below.

TABLE I

Inhibition of GABA-uptake in synaptosomes and Isoniazid antagonism.

| Comp No | GABA-Uptake Inhibition IC$_{50}$ (μM) | Isoniazid ED$_{50}$ (μmol/kg) |
| --- | --- | --- |
| 6a (+)or(S)-form | >300 | nt |
| 6b (−)or(R)-form | 120 | nt |
| 6c (+)-form | 42 | >320. |
| 6d (−)-form | >300 | nt |
| 8a | 65 | >320 |
| 8b | 0.24 | 110. |
| 8c | 120 | >120. |
| 8d | 210 | >140. |
| 8e | 100 | >300 |
| 8f | 100 | 320. |
| 8g | 0.17* | 56. |
| 8h | 4.8* | 150. |
| 8i | 0.14 | 310. |
| 8j | 1.1 | NOT DETERM |
| 8k | nt | 68. |
| 8l | nt | 71. |
| 8m | nt | 27. |
| 8n | nt | 44. |
| 8o | nt | 50. |
| 8p | nt | 30. |
| 9a | 180 | >140. |
| 11a | 0.73 | 67. |

TABLE I-continued

Inhibition of GABA-uptake in synaptosomes and Isoniazid antagonism.

| Comp No | GABA-Uptake Inhibition IC$_{50}$ ($\mu$M) | Isoniazid ED$_{50}$ ($\mu$mol/kg) |
|---|---|---|
| 11b | 0.41 | 640. |
| 14a | >300 | 86. |
| 14b | >300 | 220. |
| 15a | 70 | >120. |
| 15b | 80 | 72. |
| 15c | 84* | >120. |
| 16a | 4.5 | 55. |
| 16b | 4.9 | 81. |
| 16c | 0.36 | 160. |
| 16d | 0.31 | 63. |
| 18a | 280 | NT |
| 20a | 0.37 | 97. |
| 20b | 0.14 | nt |
| 20c | 0.17 | nt |
| 26a | >300 | NT |
| 28a | nt | 200. |
| 31a | nt | 210. |
| 31b | 300* | 55. |
| 31c | nt | 210. |
| 31d | nt | nt |
| 41a | 140 | 77. |
| 41b | 22 | >190. |

* = Preliminary Data

Furthermore, some of the compounds of the invention have been tested for inhition of neuronal and glial GABA-uptake, respectively, by the method described by Falch et. al, *Drug Dev. Res.*, 1990,21, 169–188. These tests showed that some of the compounds predominantly inhibit the glial uptake. Finally, some of the compounds have shown effect in other convulsion models.

It appears from the above table that some of the compounds of the invention which do not inhibit the GABA uptake in vitro show effect in the Isoniazide antagonism test in vivo indicating that these compounds are prodrugs.

Accordingly, the compounds of the invention are considered useful in the treatment of diseases associated with GABA neurotransmission, e.g. as analgesic, antipsychotic, anticonvulsant, or anxiolytic drugs or as drugs for the treatment of muscular and movement disorders, such as antispastics or antisymptomatics in Huntington's disease or Parkinsonism.

Formulation Examples

The pharmaceutical formulations of the invention may be prepared by conventional methods in the art. Tablets may e.g. be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavorings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of Compound 20a calculated as the free base:

| Compound 20a | 5.0 mg |
|---|---|
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 50 mg of Compound 8b calculated as the free base:

| Compound 8b | 0.5 mg |
|---|---|
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| Compound 11a | 25 mg |
|---|---|
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |

4) Solution for injection containing per millilitre:

| Compound 14a | 10 mg |
|---|---|
| Sorbitol | 5.1 mg |
| Acetic acid | 0.08 mg |
| Water for injection | ad 1 ml |

We claim:

1. An 4-aminotetrahydrobenzisoxazole or 4-aminotetrahydrobenzoisothiazole compounds having general formula I:

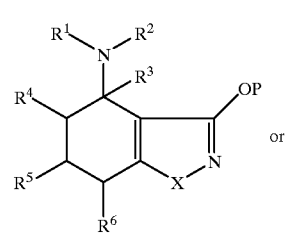

Ia or

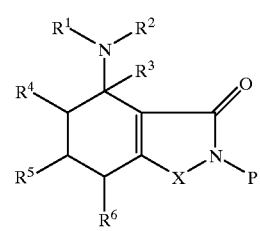

Ib wherein R$^1$ and R$^2$ are independently selected from the group consisting of:

A) hydrogen, cycloalkyl, phenyl, or a group

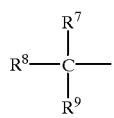

where $R^7$, $R^8$ and $R^9$ are independently selected from the group consisting of hydrogen, lower alkyl, lower alkenyl, lower alkynyl, lower alkoxy-lower alkyl, cycloalkyl, cycloalkyl-lower alkyl, phenyl, phenyl-lower alkyl, phenoxy-lower alkyl and heteroaryl selected from 2-thienyl, 3-thienyl, 2-furyl, 3-furyl, imidazolyl, oxazolyl, pyrazolyl, pyrimidinyl, pyrrolyl, thiazolyl, 1,2,4-triazolyl, 2-pyridyl, 3-pyridyl or 4-pyridyl, any phenyl or heteroaryl group present optionally being substituted with one or two substituents selected from halogen, lower alkyl, lower alkoxy, hydroxy, nitro, lower alkylthio, lower alkylsulfonyl, lower alkyl- or di(lower)alkylamino, cyano, trifluoromethyl, trifluoromethylthio, trifluoromethylsulfonyloxy and phenyl which again may be substituted with halogen, methyl, methoxy or trifluoromethyl; and any alkyl group present being optionally substituted with one to three hydroxy groups which again are optionally esterified with a $C_{2-18}$ carboxylic acid;

B) a group of general formula $Y-(CH_2)_r-(CHR^{11})_s-(CH_2)_t-$ wherein Y is selected from the following groups (1)–(5):

(1)

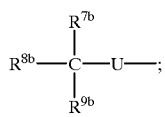

(2)

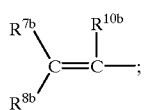

(3)

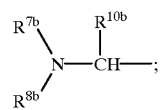

(4)

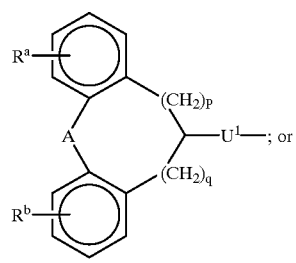

(5)

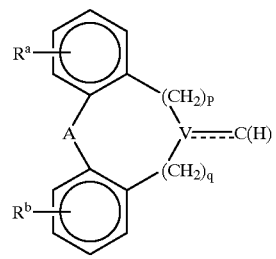

wherein U is $CHR^{10b}$, $NR^{10b}$, O or S; $U^1$ is $NR^{10b}$, O or S; p is 0 or 1; q is 0 or 1;

V is C or N and the dotted line repressents a bond when V is C and no bond when V is N;

A is O, S, $CH_2$, $(CH_2)_2$, $CH=CH-CH_2$, $(CH_2)_3$, $CH=CH$ or $O-CH_2$;

$R^a$ and $R^b$ each represent one or more substituents selected from halogen, lower alkyl, lower alkoxy, hydroxy, nitro, lower alkylthio, lower alkylsulfonyl, lower alkyl- or di(lower alkyl)amino, cyano, trifluoromethyl, trifluoromethylsulfonyloxy and trifluoromethylthio;

r and t are independently 0, 1, 2 or 3, s is 0 or 1, provided that when Y is a group (1) wherein U is $NR^{10b}$, O or S or a group (4), then r+s+t is at least 2; and when Y is a group (3) or a group (5) where V is N, then r+s+t is at least 1; $R^{7b}$, $R^{8b}$ and $R^{9b}$ are as defined for $R^7$, $R^8$ and $R^9$ in A) provided that they are not at the same time selected from hydrogen, lower alkyl, lower alkenyl and lower alkynyl;

$R^{10b}$ and $R^{11}$ are independently hydrogen, lower alkyl, lower alkenyl or lower alkynyl; and C) a group of general formula 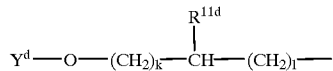 wherein n is 1, 2 or 3, m is 2 or 3; W is O or S; and $Y^c$ is a group (1)–(5) as defined in B) provided that n may not be 1, when $Y^c$ is a group (1) or (4) wherein U or $U^1$, respectively, is $NR^{10b}$, S or O;

D) a group of general formula $$Y^d-O-(CH_2)_k-\overset{R^{11d}}{\underset{}{CH}}-(CH_2)_l-$$

wherein k is 0, 1, 2 or 3;

e is 0, 1, 2 or 3; $R^{11d}$ is as defined for $R^{11}$ in B) above; and $Y^d$ is selected from the groups (2) and (5) as defined in B) above and the following groups (6)–(10):

(6)

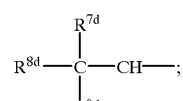

(7)

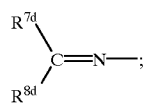

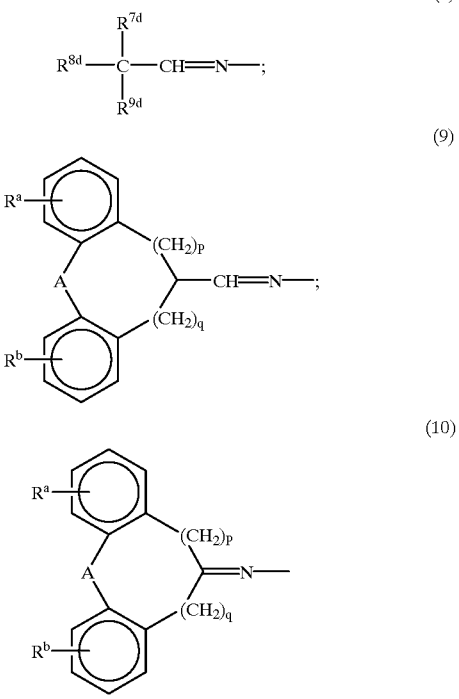

Wherein p, q, $R^a$, $R^b$, and A are as defined in B) and $R^{7d}$–$R^{11d}$ are as defined for $R^{7b}$–$R^{10b}$ and $R^{11}$, respectively, under B) or $R^1$ and $R^2$ together designate alkylene thereby forming a 4–8 membered nitrogen containing ring; or one of $R^1$ and $R^2$ is a group $R^{2'}$OCO wherein $R^{2'}$ is phenyl, or heteroaryl as defined in A) above or phenyl or such heteroaryl substituted with one or more substituents selected from halogen, lower alkyl, lower alkoxy, hydroxy, nitro, lower alkylthio, lower alkylsulfonyl, lower alkyl- or di(lower)alkylamino, cyano, trifluoromethyl, trifluoromethylthio, trifluoromethylsulfonyloxy, phenyl and phenyl substituted with halogen, methyl, methoxy or trifluoromethyl;

$R^3$–$R^6$ are independently selected from hydrogen, hydroxy and lower alkyl, any alkyl group optionally being substituted with one or two hydroxy groups;

X is oxygen

P is hydrogen or a group ZR wherein

Z is CO, CS, $SO_2$ or CR'RU, $R^t$ and $R^u$ being hydrogen, hydroxy or lower alkyl, and if Z is CO or CS, then R is selected from the groups consisting of:

i) hydrogen, $C_1$–$C_{18}$ alkyl, $C_2$–$C_{18}$ alkenyl, $C_3$–$C_8$ cycloalkyl, $C_3$–$C_8$ cycloalkenyl or $C_4$–$C_{26}$ cycloalk(en)yl-alk(en)yl, optionally substituted with one or two hydroxy groups, or phenyl optionally substituted with one or more substituents selected from the group consisting of halogen, trifluoromethyl, $C_1$–$C_4$ alkyl, $C_1$–$C_4$ alkoxy, $C_1$–$C_4$ alkylthio, $C_1$–$C_5$ acyloxy, or cyano; or ii) $QR^v$, wherein Q is O or S and $R^v$ is selected from the substituents defined for R under i) above; and iii) $NR^xR^y$, wherein $R^x$ and $R^y$ independently are selected from the substituents defined for R under i) above or $R^x$ and $R^y$ are combined to form a four to eight membered heterocyclic ring containing from one to three nitrogen atoms and from zero to three oxygen or sulfur atoms; or if Z is CR'R", R is selected from the groups consisting of:
iv) a group $QR^v$ as defined in ii);
v) a group $NR^xR^y$ as defined in iii); or
vi) a group $OC(O)R^z$, $SC(O)R^z$, $OC(S)R^z$ or $SC(S)R^z$ wherein $R^z$ is selected from the substituents defined for R under i) above;

if Z is $SO_2$, R is selected from group i) defined above;

provided that P may not be hydrogen, when $R^1$ to $R^6$ are all hydrogen, X is oxygen and the compound exists as a racemic mixture;

or a pharmaceutically acceptable salt thereof.

2. The compound of claim 1, wherein $R^1$ is lower alkenyl or alkynyl optionally substituted with hydroxy which may be esterified with a $C_{2\text{-}22}$ carboxylic acid, or phenyl or phenyl-lower alkyl, optionally substituted with halogen, lower alkyl, lower alkoxy or trifluoromethyl.

3. The compound of claim 1, wherein $R^2$ is hydrogen, lower alkyl or a group $R^{2'}$OCO.

4. The compound of claim 2 wherein P is a group ZR, wherein Z is $CH_2$ and R is a group $OC(O)R^z$.

5. A compound of claim 1, wherein $R^4$–$R^6$ are hydrogen and $R^3$ is hydrogen or lower alkyl.

6. The compound of claim 5, wherein is a compound of formula 1a.

7. The compound of claim 1, wherein $R^1$ is a group as defined under B), C) or D).

8. The compound of claim 7, wherein $R^1$ is a group as defined in B) wherein Y is a group of of formula (1) or (2) wherein U is $CH_2$ or O.

9. The compound of claim 8, wherein $R^{9b}$ is hydrogen or lower alkyl.

10. The compound of claim 8, wherein $R^{7b}$ and $R^{8b}$ are independently phenyl, phenyl substituted with halogen, lower alkyl, lower alkoxy or trifluoromethyl, 2-thienyl, 2-thienyl substituted with methyl, pyrrolyl or pyrrolyl substituted with methyl or ethyl.

11. The compound of claim 8, wherein Y is a group of formula (1), (2) or (3) wherein U is $CH_2$ or O and s is 0 and r+t is 0–5.

12. The compound of claim 1, wherein $R^4$–$R^6$ are hydrogen and $R^3$ is hydrogen or lower alkyl.

13. The compound of claim 1, wherein $R^1$ is a group as defined in B) wherein Y is a group of formula (4) or (5).

14. The compound of claim 13, wherein r+t is 0–5.

15. The compound of claim 14, wherein $R^1$ is a group of formula (5) wherein p and q are 0, A is sulfur or —$CH_2CH_2$— and $R^a$ and $R^b$ are hydrogen.

16. The compound of claim 1, wherein $R^4$–$R^6$ are hydrogen and $R^3$ is hydrogen or lower alkyl.

17. The compound of claim 8, wherein $R^1$ is a group as defined in C), and $Y^c$ is a group of formula (1) where U is $CH_2$, or a group of formula (2) in which formulas $R^{7b}$ and $R^{8b}$ are phenyl, heteroaryl or substituted phenyl or heteroaryl.

18. The compound of claim 1, wherein $R^{9b}$ is hydrogen or lower alkyl.

19. The compound of claim 1, wherein $R^1$ is a group as defined in C) wherein $Y^c$ is a group of formula (5).

20. The compound of claim 8, wherein $R^1$ is a group as defined in D) wherein $Y^d$ is a group of formula (2), (5),(6), (7), (8), (9) or (10).

21. The compound of claim 20, wherein $Y^d$ is a group of formula (6), (7) or (8), $R^{9d}$ is hydrogen or lower alkyl, $R^{10d}$ and $R^{11d}$ are hydrogen and $R^{7d}$ and $R^{8d}$ are phenyl, phenyl substituted with halogen, lower alkyl, lower alkoxy or trifluoromethyl, 2-thienyl, 2-thienyl substituted with lower alkyl, pyrrolyl or pyrrolyl substituted with methyl or ethyl.

22. The compound of claim 21, wherein is 0–4, preferably 1–3.

23. The compound of claim 8, wherein $R^2$ is hydrogen, lower alkyl or a group $R^{2'}$—O—CO— wherein $R^{2'}$ is as defined in claim 1.

24. The compound of claim 23, wherein $R^2$ is hydrogen or lower alkyl.

25. The compound of claim 1, wherein P is hydrogen.

26. A compound of claim 1 having formula 1a wherein P is a group ZR and Z is $CH_2$ and R is a group $OC(O)R^z$, pivaloyloxy or benzoyloxy.

27. A pharmaceutical composition comprising at least one 4-amino-tetrahydrobenzisoxazole or 4-amino-tetrahydrobenzisothiazole of claim 1 in a therapeutically effective amount together with a pharmaceutically acceptable carrier and or diluent.

28. A method of treating a subject suffering from disease associated with GABA transmission which comprises administering to the subject an amount of a 4-aminotetrahydrobenzisoxazole or 4-amino-tetrahydrobenzisothiazole of claim 1 effective to treat the subject.

29. A method of treating a subject suffering from analgesia, psychosis, convulsions epilepsy, anxiety, muscular and movement disorders, spastic disorders or symptoms of Huntington's or Parkinsons disease, which comprises administering an amount of a 4-aminotetrahydrobenzisoxazole or 4-amino-tetrahydrobenzisothiazole of claim 1, effective to treat the subject.

* * * * *

UNITED STATES PATENT AND TRADEMARK OFFICE
CERTIFICATE OF CORRECTION

PATENT NO.   : 5,998,613
DATED        : December 7, 1999
INVENTOR(S)  : Erik Falch et al.

It is certified that error appears in the above-identified patent and that said Letters Patent is hereby corrected as shown below:

IN THE CLAIMS
Column 34,
Line 39, delete "An" and replace with --A--
Line 39, delete "or"
Line 40, delete "4-aminotetrahydrobenzisoxazole compounds" and replace with --compond--
Line 41, delete "1" and replace with --1a or 1b--

Column 36,
Line 17, delete "represents" and replace with --represents--
Line 22, before "halogen" insert --hydrogen,--
Line 37, before "general" insert --the--
Line 43, before "general" insert --the--

Column 37,
Line 32, delete "$R^{7d}$-$R^{11d}$" and replace with --$R^{7d}$-$R^{10d}$ and $R^{11d}$--

Column 38,
Line 12, delete "X is oxygen"
Line 31, delete the second "of"
Line 33, delete "8" and replace with --18--
Lines 33-34, delete "or lower alkyl"
Lines 43-44, delete "$R^4$-$R^6$ are hydrogen and"
Line 45, delete "1" and replace with --8--

Column 39,
Line 4, before "is" insert --k+e--
Lines 4-5, delete ",preferably 1-3"
Line 12, delete "1" and replace with --7--
Lines 16-17, delete "or 4-aminotetrahydrobenzisothiazole"

UNITED STATES PATENT AND TRADEMARK OFFICE
CERTIFICATE OF CORRECTION

PATENT NO. : 5,998,613
DATED : December 7, 1999
INVENTOR(S) : Erik Falch et al.

It is certified that error appears in the above-identified patent and that said Letters Patent is hereby corrected as shown below:

Column 40,
Lines 6-7, delete "or 4-aminotetrahydrobenzisothiazole"
Lines 13-14, delete "or 4-aminotetrahydrobenzisothiazole"

Signed and Sealed this

Third Day of July, 2001

*Attest:*

*Attesting Officer*

NICHOLAS P. GODICI
*Acting Director of the United States Patent and Trademark Office*